United States Patent
Brooijmans et al.

(10) Patent No.: US 10,202,365 B2
(45) Date of Patent: Feb. 12, 2019

(54) 2-(PYRIDIN-3-YL)-PYRIMIDINE DERIVATIVES AS RET INHIBITORS

(71) Applicant: BLUEPRINT MEDICINES CORPORATION, Cambridge, MA (US)

(72) Inventors: Natasja Brooijmans, Boston, MA (US); Lucian V. DiPietro, Gloucester, MA (US); Paul E. Fleming, Wellesley, MA (US); Joseph L. Kim, Wayland, MA (US); Steven Mark Wenglowsky, Cambridge, MA (US); Yulian Zhang, Acton, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

(21) Appl. No.: 15/548,925

(22) PCT Filed: Feb. 5, 2016

(86) PCT No.: PCT/US2016/016808
§ 371 (c)(1),
(2) Date: Aug. 4, 2017

(87) PCT Pub. No.: WO2016/127074
PCT Pub. Date: Aug. 11, 2016

(65) Prior Publication Data
US 2018/0022731 A1    Jan. 25, 2018

Related U.S. Application Data

(60) Provisional application No. 62/112,897, filed on Feb. 6, 2015.

(51) Int. Cl.
| | | |
|---|---|---|
| A61K 31/506 | (2006.01) | |
| C07D 401/14 | (2006.01) | |
| C07D 403/12 | (2006.01) | |
| C07D 405/14 | (2006.01) | |
| C07D 403/04 | (2006.01) | |
| C07D 417/14 | (2006.01) | |
| A61K 45/06 | (2006.01) | |

(52) U.S. Cl.
CPC .......... *C07D 401/14* (2013.01); *A61K 31/506* (2013.01); *A61K 45/06* (2013.01); *C07D 403/04* (2013.01); *C07D 403/12* (2013.01); *C07D 405/14* (2013.01); *C07D 417/14* (2013.01)

(58) Field of Classification Search
CPC .......................... A61K 31/506; C07D 401/14
USPC .......................................... 514/256; 544/328
See application file for complete search history.

(56) References Cited

U.S. PATENT DOCUMENTS 8,802,697 B2    8/2014  Bifulco, Jr. et al.
9,126,951 B2    9/2015  Bifulco, Jr. et al.
9,200,002 B2    12/2015 Hodous et al.
9,216,172 B2    12/2015 Kohno et al.
9,297,011 B2    3/2016  Downing et al.
9,334,263 B2    5/2016  Hodous et al.
9,340,514 B2    5/2016  Bifulco, Jr. et al.
9,434,700 B2    9/2016  Bifulco, Jr. et al.
9,499,522 B2    11/2016 DiPietro et al.
9,688,680 B2    6/2017  Hodous
9,695,165 B2    7/2017  Bifulco, Jr. et al.
9,884,861 B2    2/2018  Hodous et al.
9,944,651 B2    4/2018  Hodous et al.
9,994,552 B2    6/2018  DiPietro et al.
9,994,575 B2    6/2018  Hodous et al.
10,000,490 B2   6/2018  Bifulco, Jr. et al.
10,000,496 B2   6/2018  Hodous et al.
10,017,512 B2   7/2018  Wenglowsky et al.
2012/0316137 A1 12/2012 Huang et al.
2013/0096136 A1 4/2013  Hata et al.
2013/0115313 A1 5/2013  Charrier et al.
2013/0116280 A1 5/2013  Ju et al.
(Continued)

FOREIGN PATENT DOCUMENTS

CN    105255927 A    1/2016
EP    3037547 A1     6/2016
(Continued)

OTHER PUBLICATIONS

Arighi, E. et al. (2005) "RET tyrosine kinase signaling in development and cancer" *Cytokine & Growth Factor Reviews*, 16:441-467.
Brandt, W. et al. (2010) "Inhibitors of the RET tyrosine kinase based on a 2-(alkylsulfanyl)-4-(3-thienyl) nicotinonitrile scaffold" *Eur J Med Chem*, 45:2919-2927.
International Search Report and Written Opinion dated Apr. 29, 2016, in International Patent Application No. PCT/US2016/016808, filed Feb. 5, 2016, by Blueprint Medicines Corp. (8 pages).
International Search Report and Written Opinion dated Jan. 18, 2017, in International Patent Application No. PCT/US2016/059879, filed Nov. 1, 2016, by Blueprint Medicines Corp. (12 pages).
(Continued)

*Primary Examiner* — Jeffrey H Murray
(74) *Attorney, Agent, or Firm* — Finnegan, Henderson, Farabow, Garrett & Dunner, LLP

(57) ABSTRACT

Described herein are compounds, such as compounds of Formula (I) and pharmaceutically acceptable salts thereof, that inhibit wild-type RET and its resistant mutants, pharmaceutical compositions including such compounds, and methods of using such compounds and compositions, e.g., for treating a condition mediated by aberrant RET activity (I)

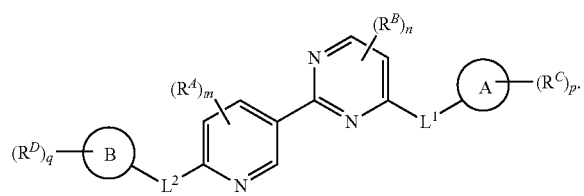

15 Claims, No Drawings

(56) References Cited

U.S. PATENT DOCUMENTS

| | | | |
|---|---|---|---|
| 2014/0187559 | A1 | 7/2014 | Miduturu |
| 2014/0221404 | A1 | 8/2014 | Kohno et al. |
| 2014/0272951 | A1 | 9/2014 | Chakravarti et al. |
| 2015/0057335 | A1 | 2/2015 | Kohno et al. |
| 2015/0177246 | A1 | 6/2015 | Shibata et al. |
| 2016/0102097 | A1 | 4/2016 | Hodous et al. |
| 2017/0014413 | A1 | 1/2017 | Downing et al. |
| 2017/0022206 | A1 | 1/2017 | Hodous et al. |
| 2017/0029409 | A1 | 2/2017 | DiPietro et al. |
| 2017/0057953 | A1 | 3/2017 | Hodous et al. |
| 2017/0066773 | A1 | 3/2017 | Wenglowsky et al. |
| 2017/0066812 | A1 | 3/2017 | Bifulco, Jr. et al. |
| 2017/0121312 | A1 | 5/2017 | Brubaker et al. |
| 2017/0145018 | A1 | 5/2017 | Wenglowsky et al. |
| 2017/0174652 | A1 | 6/2017 | Bifulco, Jr. et al. |
| 2017/0204104 | A1 | 7/2017 | Hodous et al. |
| 2017/0253593 | A1 | 9/2017 | Bifulco, Jr. et al. |
| 2017/0267661 | A1 | 9/2017 | Kim et al. |
| 2017/0298069 | A1 | 10/2017 | Brooijmans et al. |
| 2018/0022732 | A1 | 1/2018 | Brubaker et al. |
| 2018/0030032 | A1 | 2/2018 | Brubaker et al. |

FOREIGN PATENT DOCUMENTS

| | | |
|---|---|---|
| JP | 2015-109806 A | 6/2015 |
| WO | WO 01/60816 A1 | 8/2001 |
| WO | WO 2004/009087 A1 | 1/2004 |
| WO | WO 2007/023382 A2 | 3/2007 |
| WO | WO 2009/003136 A1 | 12/2008 |
| WO | WO 2009/007748 A2 | 1/2009 |
| WO | WO 2009/014637 A2 | 1/2009 |
| WO | WO 2009/100536 A1 | 8/2009 |
| WO | WO 2011/060295 A1 | 5/2011 |
| WO | WO 2014/039971 A1 | 3/2014 |
| WO | WO 2014/050781 A1 | 4/2014 |
| WO | WO 2014/072220 A1 | 5/2014 |
| WO | WO 2014/130810 A1 | 8/2014 |
| WO | WO 2014/141187 A1 | 9/2014 |
| WO | WO 2015/006875 A1 | 1/2015 |
| WO | WO 2015/079251 A1 | 6/2015 |
| WO | WO 2016/037578 A1 | 3/2016 |
| WO | WO 2016/038552 A1 | 3/2016 |
| WO | WO 2016/075224 A1 | 5/2016 |
| WO | WO 2016/127074 A1 | 8/2016 |
| WO | WO 2017/011776 A1 | 1/2017 |
| WO | WO 2017/079140 A1 | 5/2017 |
| WO | WO 2017/161269 A1 | 9/2017 |
| WO | WO 2018/017983 A1 | 1/2018 |
| WO | WO 2018/022761 A1 | 2/2018 |
| WO | WO 2018/049233 A9 | 7/2018 |

OTHER PUBLICATIONS

International Search Report and Written Opinion dated Jun. 12, 2017, in International Patent Application No. PCT/US2017/022969, filed Mar. 17, 2017, by Blueprint Medicines Corp. (12 pages).
Kuster, B. (Ed.) (2012) *Kinase inhibitors. Methods and Protocols.* Humana Press; Chapters 1 and 2, pp. 1-44.
Mologni, L. et al. (2010) "Synthesis, structure-activity relationship and crystallographic studies of 3-substituted indolin-2-one RET inhibitors" *Bioorg Med Chem*, 18:1482-1496.
Mologni, L. et al. (2013) "Ponatinib is a potent inhibitor of wild-type and drug-resistant gatekeeper mutant RET kinase" *Mol Cell Endocrinol*, 377:1-6.
Mologni, L. et al. (2017) "RET kinase inhibitors: a review of recent patents (2012-2015)" *Exp Opin Ther Patents*, 27(1):91-99.
Notice of Allowance dated Sep. 26, 2017, in U.S. Appl. No. 15/093,354, filed Apr. 7, 2016, by Blueprint Medicines Corp.
Notice of Allowance dated Sep. 5, 2017, in U.S. Appl. No. 15/217,503, filed Jul. 22, 2016, by Blueprint Medicines Corp.
Notice of Allowance dated Aug. 3, 2017, in U.S. Appl. No. 15/479,145, filed Apr. 4, 2017, by Blueprint Medicines Corp.
Notice of Allowance dated Oct. 25, 2017, in U.S. Appl. No. 15/340,428, filed Nov. 1, 2016, by Blueprint Medicines Corp.
Plaza-Menacho, I. et al. (2014) "Mechanisms of RET signaling in cancer: Current and future implications for targeted therapy" *Cellular Signalling*, 26:1743-1752.
Robinett, R.G. et al. (2007) "The discovery of substituted 4-(3-hyroxyanilino)-quinolines as potent RET kinase inhibitors" *Bioorg Med Chem Lett*, 17:5886-5893.
U.S. Appl. No. 15/657,057, filed Jul. 21, 2017, by Brubaker et al.
U.S. Appl. No. 15/660,840, filed Jul. 26, 2017, by Brubaker et al.
Antonescu, C.R. et al. (Jul. 2015) "Molecular Characterization of Inflammatory Myofibroblastic Tumors with Frequent ALK and ROS1 Fusions and Rare Novel RET Gene Rearrangement" *Am J Surg Pathol*, 39(7):957-967. HHS Public Access Author Manuscript; available in PMC Jul. 1, 2015 (19 pages).
Baselga, J. et al. (2005) "Phase II and Tumor Pharmacodynamic Study of Gefitinib in Patients with Advanced Breast Cancer" *J Clin Oncol*, 23(23):5323-5333.
Caprelsa (vandetanib) "Full Prescribing Information" Reference ID: 3964956, Cambridge, MA: Sanofi Genzyme; 2016.
Ceccherini, I. et al. (1997) "Somatic in frame deletions not involving juxtamembranous cysteine residues strongly activate the RET proto-oncogene" *Oncogene*, 14:2609-2612.
Chalice Software Technical Guide, Horizon CombinatoRx Inc., Cambridge, MA, USA (downloaded Jul. 2018).
Cometriq (cabozantinib) "Full Prescribing Information" Reference ID: 3964956, South San Francisco, CA: Exelixix, Inc.; 2018.
Druker, B.J. et al. (2001) "Efficacy and Safety of a Specific Inhibitor of the BCR-ABL Tyrosine Kinase in Chronic Myeloid Leukemia" *New Engl J Med*, 344(14):1031-1037.
Eisenhauer, E.A. et al. (2009) "New response evaluation criteria in solid tumours: Revised RECIST guideline (version 1.1)" *Eur J Cancer*, 45:228-247.
Elisei, R. et al. (2008) "Prognostic Significance of Somatic RET Oncogene Mutations in Sporadic Medullary Thyroid Cancer: A 10-Year Follow-Up Study" *J Clin Endocrinol Metab*, 93(3):682-687.
Fang, P. et al. (Feb. 2016) "Detection of a novel RET gene fusion in a non-small cell lung cancer patient using AMP chemistry" *J Thorac Oncol*, 11.2:S21-S22.
Gautschi, O. et al. (2016) "Targeting RET in patients with RET-rearranged lung cancers: Results from a global registry" *J Clin Oncol*, 34(15S) (suppl; abstr 9014).
Grubbs, E.G. et al. (Mar. 2015) "RET Fusion as a Novel Driver of Medullary Thyroid Carcinoma" *J Clin Endocrinol Metab*, 100:788-793.
Halkova, T. et al. (2015) "A novel RET/PTC variant detected in a pediatric patient with papillary thyroid cancer without ionization history" *Hum Pathol*, 46:1962-1969.
Horiike, A. et al. (2016) "Sorafenib treatment for patients with RET fusion-positive non-small cell lung cancer" *Lung Cancer*, 93:43-46.
Joung, J.Y. et al. (2016) "Diffuse sclerosing variant of papillary thyroid carcinoma: major genetic alterations and prognostic implications" *Histopathology*, 69:45-53.
Jovanovic, R. et al. (2015) "Novel RET Mutations in Macedonian Patients with Medullary Thyroid Carcinoma: Genotype-Phenotype Correlations" *Prilozi*, 36(1):93-107.
Karrasch, T. et al. (2016) "How to Assess the Clinical Relevance of Novel RET Missense Variants in the Absence of Functional Studies?" *Eur Thyroid J*, 5:73-77.
Kato, S. et al. (Apr. 15, 2017) "RET Aberrations in Diverse Cancers: Next-Generation Sequencing of 4,871 Patients" *Clin Cancer Res*, 23(8):1988-1997.
Kim, S.H. et al. (2015) "A New Germline ALA641THR Variant in the Transmembrane Domain of the RET Gene Associated with Medullary Thyroid Cancer" *Acta Endocrinologica (Buc)*, 11.2:189-194.
Krampitz, G.W. and J.A. Norton (2014) "RET Gene Mutations (Genotype and Phenotype) of Multiple Endocrine Neoplasia Type 2 and Familial Medullary Thyroid Carcinoma" *Cancer*, 120:1920-1931.
Latteyer, S. et al. (Mar. 2016) "A 6-Base Pair in Frame Germline Deletion in Exon 7 of RET Leads to Increased RET Phosphorylation, ERK Activation, and MEN2A" *J Clin Endocrinol Metab*, 101(3):1016-1022.

(56) References Cited

OTHER PUBLICATIONS

Le Rolle, A. et al. (2015) "Identification and characterization of RET fusions in advanced colorectal cancer" *Oncotarget*, 6(30):28929-28937.
Lee, M.S. et al. (2016) "Efficacy of the combination of MEK and CDK4/6 inhibitors in vitro and in vivo in KRAS mutant colorectal cancer models" *Oncotarget*, 7(26):39595-39608.
Lehar, J. et al. (2009) "Synergistic drug combinations improve therapeutic selectivity" *Nat Biotechnol*, 27(7):659-666. HHS Public Access Author Manuscript; available in PMC Jan. 1, 2010 (23 pages).
Lin, J.J. et al. (2016) "Clinical Activity of Alectinib in Advanced RET-Rearranged Non-Small Cell Lung Cancer" *J Thorac Oncol*, 11(11):2027-2032.
Lipson, D. et al. (2012) "Identification of new ALK and RET gene fusions from colorectal and lung cancer biopsies" *Nat Med*, 18(3):382-384. HHS Public Access Author Manuscript; available in PMC Feb. 6, 2014 (7 pages).
Machens, A et al. (2003) "Early Malignant Progression of Hereditary Medullary Thyroid Cancer" *New Engl J Med*, 349:1517-1525.
Moura, M.M. et al. (2009) "Correlation of RET somatic mutations with clinicopathological features in sporadic medullary thyroid carcinomas" *Br J Cancer*, 100:1777-1783.
Mulligan, L.M. et al. (Jun. 3, 1993) "Germ-line mutations of the RET proto-oncogene in multiple endocrine neoplasia type 2A" *Nature*, 363:458-460.
Mulligan, L.M. et al. (1995) "Genotype-phenotype correlation in multiple endocrine neoplasia type 2: report of the International RET Mutation Consortium" *J Int Med*, 238:343-346.
Mulligan, L.M. (Mar. 2014) "RET revisited: expanding the oncogenic portfolio" *Nat Rev Cancer*, 14:173-186.
Notice of Allowance dated Jun. 5, 2018, in U.S. Appl. No. 15/340,428, filed Nov. 1, 2016, by Blueprint Medicines Corp.
Notice of Allowance dated Jun. 27, 2018, in U.S. Appl. No. 15/222,523, filed Jul. 28, 2016, by Blueprint Medicines Corp.
Notice of Allowance dated Apr. 25, 2018, in U.S. Appl. No. 15/462,255, filed Mar. 17, 2017, by Blueprint Medicines Corp.
Notice of Allowance dated Apr. 2, 2018, in U.S. Appl. No. 15/660,840, filed Jul. 26, 2017, by Blueprint Medicines Corp.
Pirker, R. and M. Filipits (2015) "Alectinib in RET-rearranged non-small cell lung cancer—Another progress in precision medicine?" *Transl Lung Cancer Res*, 4(6):797-800.
Qi, X. et al. (2015) "RET mutation p.S891A in a Chinese family with familial medullary thyroid carcinoma and associated cutaneous amyloidosis binding OSMR variant p.G513D" *Oncotarget*, 6(32):33993-34003.
Romei, C. et al. (Apr. 2016) "A comprehensive overview of the role of the RET proto-oncogene in thyroid carcinoma" *Nat Rev Endocrinol*, 12:192-202.
Saito, M. et al. (Jun. 2016) "Gene aberrations for precision medicine against lung adenocarcinoma" *Cancer Sci*, 107(6):713-720.
Sarker, D. and P. Workman (2007) "Pharmacodynamic Biomarkers for Molecular Cancer Therapeutics" *Adv Cancer Res*, 96:213-268.
Scollo, C. et al. (2016) "A novel RET gene mutation in a patient with apparently sporadic pheochromocytoma" *Endocr J*, 63(1):87-91.
Silva, A.L. et al. (2015) "Identification and characterization of two novel germline RET variants associated with medullary thyroid carcinoma" *Endocrine*, 49:366-372.
Suehara, Y. et al. (Dec. 15, 2012) "Identification of KIF5B-RET and GOPC-ROS1 fusions in lung adenocarcinomas through a comprehensive mRNA-based screen for tyrosine kinase fusions" *Clin Cancer Res*, 18(24):6599-6608. HHS Public Access Author Manuscript; available in PMC Nov. 17, 2014 (18 pages).
Stransky, N. et al. (2014) "The landscape of kinase fusions in cancer" *Nat Commun*, 5:4846 (10 pages).
Takeuchi, K. et al. (Mar. 2012) "RET, ROS1 and ALK fusions in lung cancer" *Nat Med*, 18(3):378-381.
Tan, D.S. et al. (2009) "Biomarker-Driven Early Clinical Trials in Oncology" *Cancer J*, 15(5):406-420.

U.S. Nat'l Library of Med., *A Phase 1 Trial of Vandetanib (a Multi-kinase Inhibitor of EGFR, VEGFR and RET Inhibitor) in Combination With Everolimus (an mTOR Inhibitor) in Advanced Cancer*, ClinicalTrials.gov, https://clinicaltrials.gov/ct2/show/NCT01582191 (last updated Jul. 3, 2018) (7 pages).
U.S. Nat'l Library of Med., *Phase 1 Study of the Highly-selective RET Inhibitor BLU-667 in Patients With Thyroid Cancer, Non-Small Cell Lung Cancer, and Other Advanced Solid Tumors*, ClinicalTrials.gov, https://clinicaltrials.gov/ct2/show/NCT03037385 (last updated Jun. 27, 2018) (8 pages).
U.S. Appl. No. 15/867,637, filed Jan. 10, 2018, by Blueprint Medicines Corp.
U.S. Appl. No. 15/973,340, filed May 7, 2018, by Blueprint Medicines Corp.
U.S. Appl. No. 15/973,378, filed May 7, 2018, by Blueprint Medicines Corp.
U.S. Appl. No. 16/002,587, filed Jun. 7, 2018, by Blueprint Medicines Corp.
U.S. Appl. No. 16/027,166, filed Jul. 3, 2018, by Blueprint Medicines Corp.
Wang, L. et al. (2012) "Identification of a Novel, Recurrent HEY1-NCOA2 Fusion in Mesenchymal Chondrosarcoma based on a Genome-wide Screen of Exon-level Expression Data" *Genes Chromosomes Cancer*, 51(2):127-139. HHS Public Access Author Manuscript; available in PMC Feb. 1, 2013 (24 pages).
Wang, R. et al. (Dec. 10, 2012) "RET Fusions Define a Unique Molecular and Clinicopathologic Subtype of Non-Small-Cell Lung Cancer" *J Clin Oncol*, 30(35):4352-4359.
Wells, S.A. et al. (2015) "Revised American Thyroid Association Guidelines for the Management of Medullary Thyroid Carcinoma" *Thyroid*, 25(6):567-610.
Abdel-Rahman, O. and M. Fouad (2014) "Risk of cardiovascular toxicities in patients with solid tumors treated with sunitinib. axitinib, cediranib or regorafenib: an updated systematic review and comparative meta-analysis" *Crit Rev Oncol Hematol*, 92:194-207.
Bentzien, F. et al. (2013) "In Vitro and in Vivo Activity of Cabozantinib (XL184), an Inhibitor of RET, MET, and VEGFR2, in a Model of Medullary Thyroid Cancer" *Thyroid*, 23(12):1569 1577.
Carlomagno, F et al. (Feb. 1995) "Point Mutation of the Ret Proto-oncogene in the TT Human Medullary Thyroid Carcinoma Cell Line" *Biochem Biophys Res Common*, 207(3):1022-1028.
Evans, E. (May 1, 2016) "The Development of Potent and Selective RET Inhibitors" Slides presented at the 2016 Annual Meeting of the International Thyroid Oncology Group at the University of Colorado (19 pages).
Hayashi, H. et al. (2000) "Characterization of intracellular signals via tyrosine 1062 in RET activated by glial cell line-derived neurotrophic factor" *Oncogene*, 19:4469-4475.
International Search Report and Written Opinion dated Oct. 12, 2017, in International Patent Application No. PCT/US2017/043964, filed Jul. 26, 2017, by Blueprint Medicines Corp. (13 pages).
International Search Report and Written Opinion dated Oct. 25, 2017, in International Patent Application No. PCT/US2017/043340, filed Jul. 21, 2017, by Blueprint Medicines Corp. (14 pages).
Notice of Allowance dated Jan. 17. 2018, in U.S. Appl. No. 14/887,614, filed Oct. 20, 2015, by Blueprint Medicines Corp.
Notice of Allowance dated Jan. 16, 2018, in U.S. Appl. No. 15/217,503, filed Jul. 22, 2016, by Blueprint Medicines Corp.
Notice of Allowance dated Dec. 15, 2017, in U.S. Appl. No. 15/462,255, filed Mar. 17, 2017, by Blueprint Medicines Corp.
Notice of Allowance dated Nov. 30, 2017, in U.S. Appl. No. 15/479,145, filed Apr. 4, 2017, by Blueprint Medicines Corp.
Notice of Allowance dated Jan. 17, 2018, in U.S. Appl. No. 15/660,840, filed Jul. 26, 2017, by Blueprint Medicines Corp.
Rahal, R. et al. (2016) "The development of potent, selective RET inhibitors that target both wild-type RET and prospectively identified resistance mutations to multi-kinase inhibitors" Abstract submitted to the American Association for Cancer Research (AACR) Annual Meeting, Apr. 16-20, 2016, New Orleans; submission date Dec. 1, 2015 (2 pages).

(56) References Cited

OTHER PUBLICATIONS

Rahal, R. (Apr. 18, 2016) "The development of potent, selective RET inhibitors" Slides of a Presentation at the American Association for Cancer Research (AACR) Annual Meeting, Apr. 16-20, 2016. New Orleans (15 pages).
Suzuki, M. et al. (Jul. 2013) "Identification of a lung adenocarcinoma cell line with CCDC6-RET fusion gene and the effect of RET inhibitors in vitro and in vivo" *Cancer Sci*, 104(7):896-903.
Touat, M. et al. (2015) "Targeting FGFR Signaling in Cancer" *Clin Cancer Res*, 21(12):2684-2694.

2-(PYRIDIN-3-YL)-PYRIMIDINE DERIVATIVES AS RET INHIBITORS

CROSS-REFERENCE TO RELATED APPLICATIONS

This application is a U.S. national phase entry under 35 U.S.C. § 371 from PCT International Application No. PCT/US2016/016808, filed on Feb. 5, 2016, which claims the benefit of priority from U.S. Provisional Patent Application No. 62/112,897, filed on Feb. 6, 2015. The entire contents of the above applications are incorporated herein by reference in their entireties.

This invention relates to inhibitors of RET that are active against wild-type RET and its resistant mutants.

BACKGROUND

RET is a receptor tyrosine kinase that activates multiple downstream pathways involved in cell proliferation and survival. RET fusions are implicated in several cancers including papillary thyroid carcinoma and non-small cell lung cancer. A genomics analysis on the landscape of kinase fusions identified RET fusions in breast and colon cancer patient samples, providing therapeutic rationale for the use of RET inhibitors in multiple patient subpopulations.

The identification of RET fusions as drivers in some cancers prompted the use of approved multi-kinase inhibitors with RET inhibitory activity to treat patients whose tumors express a RET fusion protein. However, these drugs cannot always be dosed at the levels required to sufficiently inhibit RET due to toxicities that result from inhibition of targets other than RET. Further, one of the greatest challenges in treating cancer is the ability of tumor cells to become resistant to therapy. Kinase reactivation via mutation is a common mechanism of resistance. When resistance occurs, the patient's treatment options are often very limited, and the cancer progresses, unchecked, in most instances. There is thus a need for compounds that inhibit RET, as well as its resistant mutants.

SUMMARY

In one aspect, the invention features a compound of Formula (I) or a pharmaceutically acceptable salt thereof, wherein:

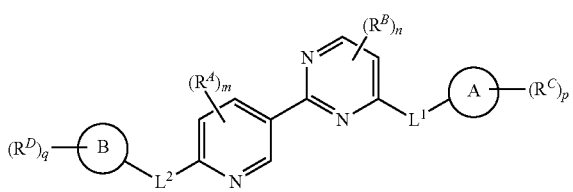

(I)

Rings A and B are each independently selected from aryl, heteroaryl, cycloalkyl and heterocyclyl;

each $L^1$ and $L^2$ is independently selected from a bond, —($C_1$-$C_6$ alkylene)-, —($C_2$-$C_6$ alkenylene)-, —($C_2$-$C_6$ alkynylene)-, —($C_1$-$C_6$ haloalkylene)-, —($C_1$-$C_6$ heteroalkylene)-, —C(O)—, —O—, —S—, —S(O), —S(O)$_2$—, —N($R^1$)—, —O—($C_1$-$C_6$ alkylene)-, —($C_1$-$C_6$ alkylene)-O—, —N($R^1$)—C(O)—, —C(O)—N($R^1$)—, —($C_1$-$C_6$ alkylene)-N($R^1$)—, —N($R^1$)—($C_1$-$C_6$ alkylene)-, —N($R^1$)—C(O)—($C_1$-$C_6$ alkylene)-, —($C_1$-$C_6$ alkylene)-N($R^1$)—C(O)—, —C(O)—N($R^1$)—($C_1$-$C_6$ alkylene)-, —($C_1$-$C_6$ alkylene)-C(O)—N($R^1$)—, —N($R^1$)—S(O)$_2$—, —S(O)$_2$—N($R^1$)—, —N($R^1$)—S(O)$_2$—($C_1$-$C_6$ alkylene)-, and —S(O)$_2$—N($R^1$)—($C_1$-$C_6$ alkylene)-; wherein each alkylene, alkenylene, alkynylene, haloalkylene, and heteroalkylene is independently substituted with 0-5 occurrences of R';

each $R^A$ and $R^B$ is independently selected from $C_1$-$C_6$ alkyl, $C_1$-$C_6$ alkoxy, halo, $C_1$-$C_6$ haloalkyl, $C_1$-$C_6$ hydroxyalkyl, $C_1$-$C_6$ heteroalkyl, and —N($R^1$)($R^1$); wherein each alkyl, alkoxy, haloalkyl, hydroxyalkyl, and hydroxyalkyl is independently substituted with 0-5 occurrences of $R^a$;

each $R^C$ and $R^D$ is independently selected from $C_1$-$C_6$ alkyl, $C_2$-$C_6$ alkenyl, $C_2$-$C_6$ alkynyl, $C_1$-$C_6$ alkoxy, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —($C_1$-$C_6$ alkylene)-C(O)$R^1$, —S$R^1$, —S(O)$_2R^1$, —S(O)$_2$—N($R^1$)($R^1$), —($C_1$-$C_6$ alkylene)-S(O)$_2R^1$, —($C_1$-$C_6$ alkylene)-S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, —($C_1$-$C_6$ alkylene)-N($R^1$)—C(O)$R^1$, —N($R^1$)S(O)$_2R^1$, and —P(O)($R^1$)($R^1$); wherein each of alkyl, alkenyl, alkynyl, alkoxy, heteroalkyl, haloalkyl, haloalkoxy, hydroxyalkyl, cycloalkyl, aryl, heteroaryl, aryloxy, aralkyl, heterocyclyl, and heterocyclylalkyl is independently substituted with 0-5 occurrences of $R^a$; or 2 $R^C$ or 2 $R^D$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, $C_1$-$C_6$ alkyl, $C_1$-$C_6$ thioalkyl, $C_1$-$C_6$ alkoxy, $C_1$-$C_6$ haloalkyl, $C_1$-$C_6$ hydroxyalkyl, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxy, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

each $R^a$ and $R^b$ is independently $C_1$-$C_6$ alkyl, halo, hydroxyl, $C_1$-$C_6$ haloalkyl, $C_1$-$C_6$ heteroalkyl, $C_1$-$C_6$ hydroxyalkyl, $C_1$-$C_6$ alkoxy, cycloalkyl, heterocyclyl, or cyano, wherein each of alkyl, haloalkyl, heteroalkyl, hydroxyalkyl, alkoxy, cycloalkyl and heterocyclyl is independently substituted with 0-5 occurrences of R';

each R' is $C_1$-$C_6$ alkyl, $C_1$-$C_6$ heteroalkyl, halo, hydroxyl, $C_1$-$C_6$ haloalkyl, $C_1$-$C_6$ hydroxyalkyl, cycloalkyl or cyano; or 2 R' together with the atom(s) to which they are attached form a cycloalkyl or heterocyclyl ring;

m is 0, 1, 2, or 3;

n is 0, 1, or 2; and p and q are each independently 0, 1, 2, 3, or 4.

EMBODIMENTS OF THE INVENTION

Definitions

As used herein, the terms a "patient," "subject," "individual," and "host" refer to either a human or a non-human animal suffering from or suspected of suffering from a disease or disorder associated with aberrant RET expression (i.e., increased RET activity caused by signaling through RET) or biological activity.

"Treat" and "treating" such a disease or disorder refers to ameliorating at least one symptom of the disease or disorder.

These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "preventing" when used in relation to a condition or disease such as cancer, refers to a reduction in the frequency of, or delay in the onset of, symptoms of the condition or disease. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The term "therapeutic effect" refers to a beneficial local or systemic effect in animals, particularly mammals, and more particularly humans, caused by administration of a compound or composition of the invention. The phrase "therapeutically-effective amount" means that amount of a compound or composition of the invention that is effective to treat a disease or condition caused by over expression of RET or aberrant RET biological activity at a reasonable benefit/risk ratio. The therapeutically effective amount of such substance will vary depending upon the subject and disease condition being treated, the weight and age of the subject, the severity of the disease condition, the manner of administration and the like, which can readily be determined by one of skill in the art.

As used herein, "developing resistance" means that when a drug is first administered to the patient, the patient's symptoms improve, whether measured by decrease in tumor volume, a decrease in the number of new lesions, or some other means that a physician uses to judge disease progression; however, those symptoms stop improving, or even worsen at some point. At that time, the patient is said to have developed resistance to the drug.

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —$CH_2$—, —$CH_2CH_2$—, and $CH_2CH_2CH_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like. The term "haloalkoxy" refers to an alkoxy in which one or more hydrogen atoms are replaced by halo, and includes alkoxy moieties in which all hydrogens have been replaced by halo (e.g., perfluoroalkoxy).

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkenylene" refers to an alkenyl group having two connecting points. For example, "ethenylene" represents the group —CH═CH—. Alkenylene groups can also be in an unsubstituted form or substituted form with one or more substituents.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to an alkynyl having two connecting points. For example, "ethynylene" represents the group —C≡C—. Alkynylene groups can also be in an unsubstituted form or substituted form with one or more substituents.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Haloalkyl" and "haloalkoxy" refers to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine. "Haloalkylene" refers to a divalent alkyl, e.g., —$CH_2$—, —$CH_2CH_2$—, and —$CH_2CH_2CH_2$—, in which one or more hydrogen atoms are replaced by halo, and includes alkyl moieties in which all hydrogens have been replaced by halo.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —$CH_2OCH_2CH_3$ radical is referred to as a "$C_3$" heteroalkyl. Connection to the rest of the molecule may be through either a heteroatom or a carbon in the heteroalkyl chain. "Heteroalkylene" refers to a divalent optionally substituted alkyl, which has one or more skeletal chain atoms selected from an atom other than carbon, e.g., oxygen, nitrogen, sulfur, phosphorus or combinations thereof.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a -(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In some embodiments, heterocyclyl can include:

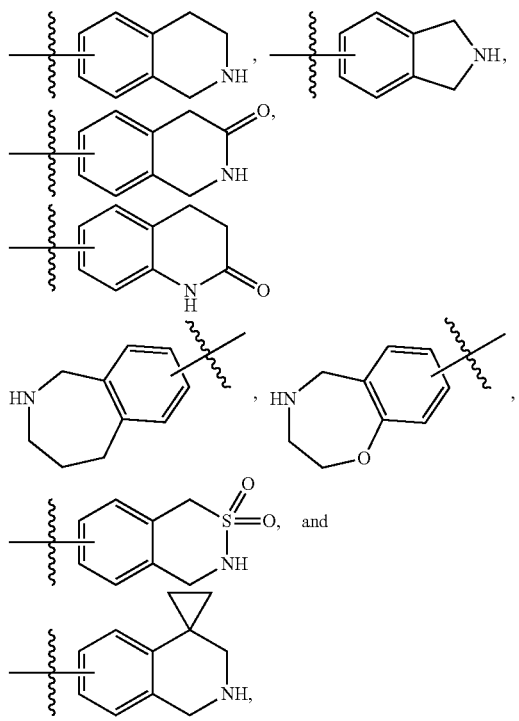

wherein the point of attachment to the base structure can be through any of the atoms on the heterocyclyl, e.g., through a carbon atom or a nitrogen atom of the heterocyclyl.

"Heterocyclylalkyl" refers to an alkyl group substituted with a heterocyclyl group.

"Cyano" refers to a —CN radical.

"Nitro" refers to —NO$_2$.

"Hydroxy" or "hydroxyl" refers to —OH.

"Hydroxyalkylene" refers to a divalent alkyl, e.g., —CH$_2$—, —CH$_2$CH$_2$—, and —CH$_2$CH$_2$CH$_2$—, in which one or more hydrogen atoms are replaced by a hydroxy, and includes alkyl moieties in which all hydrogens have been replaced by hydroxy.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

Compounds

In some embodiments of Formula I each of L$^1$ and L$^2$ is other than a bond; and the compound is other than:

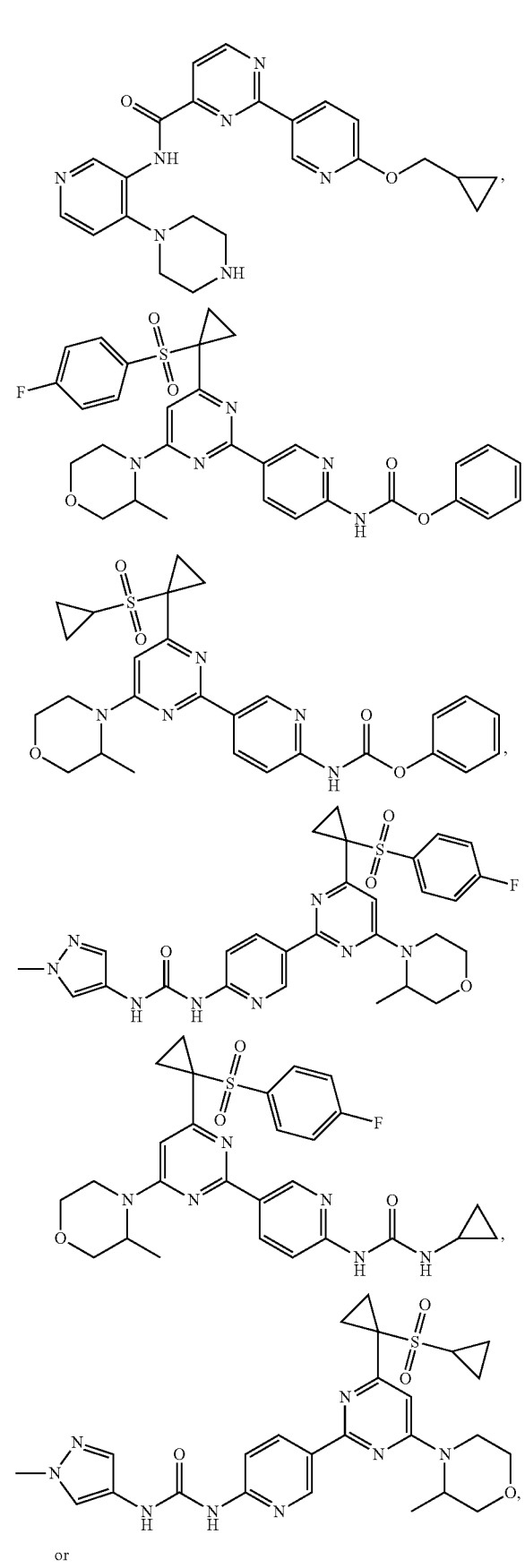

or

-continued

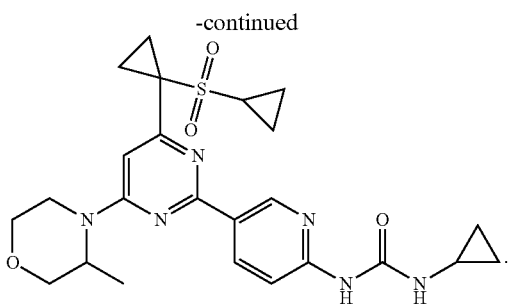

In some embodiments of Formula I, ring A is heteroaryl. In some aspects of these embodiments, ring A is 1H-pyrazolyl. In some more specific aspects of these embodiments, ring A is 1H-pyrazol-3-yl.

In some embodiments of Formula I, p is 1 or more and at least one $R^C$ is $C_1$-$C_4$ alkyl. In some aspects of these embodiments, p is 1. In some aspects of these embodiments, at least one $R^C$ is methyl. In more specific aspects of these embodiments, p is 1 and $R^C$ is methyl. In even more specific aspects of these embodiments, the portion of the compound represented by:

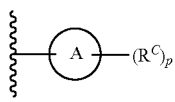

is 5-methyl-1H-pyrazol-3-yl.

In some embodiments of Formula I, $L^1$ is —N($R^1$)—C(O)-†, —N($R^1$)—($C_1$-$C_6$ alkylene)-†, or —N($R^1$)—C(O)—($C_1$-$C_6$ alkylene)-†, wherein "†" represents a portion of $L^1$ bound to ring A. In some aspects of these embodiments, $L^1$ is —N($R^1$)—. In more specific aspects of these embodiments, $L^1$ is —NH—.

In some embodiments of Formula I, $L^2$ is selected from *—C(O)—, *—N($R^1$)—C(O)— and *—($C_1$-$C_6$ alkylene)-N($R^1$)—C(O)—, wherein the $C_1$-$C_6$ alkylene portion of $L^2$ is substituted with 0-5 occurrences of R', and wherein "*" represents a portion of $L_2$ bound to ring B. In some aspects of these embodiments, $L_2$ is *—C(O)—. In other aspects of these embodiments, $L_2$ is *—N($R^1$)—C(O)—. In still other aspects of these embodiments, $L_2$ is *—($C_1$-$C_6$ alkylene)-N($R^1$)—C(O)—, wherein the $C_1$-$C_6$ alkylene portion of $L^2$ is substituted with 0-5 occurrences of R'. In certain more specific aspects of these embodiments, the compound has structural Formula I(b):

I(b)

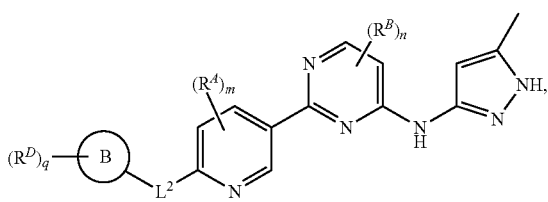

or a pharmaceutically acceptable salt thereof, wherein $L^2$ is *—($C_1$-$C_6$ alkylene)-N($R^1$)—C(O)—, each of $R^A$, $R^B$, $R^D$, ring B, m, n and q are defined as for Formula I, and wherein the $C_1$-$C_6$ alkylene portion of $L^2$ is substituted with 0-5 occurrences of R'.

In some more specific embodiments of Formula I or I(b), $L^2$ is selected from *—$CH_2$—N($R^1$)—C(O)— and *—CH($C_1$-$C_4$ alkyl)-N($R^1$)—C(O)—. In some aspects of these embodiments, $L_2$ is selected from *—$CH_2$—NH—C(O)—, *—CH($CH_3$)—NH—C(O)—, and *—CH($CH_2CH_3$)—NH—C(O)—.

In some embodiments, the invention provides a compound Formula I(c):

I(c)

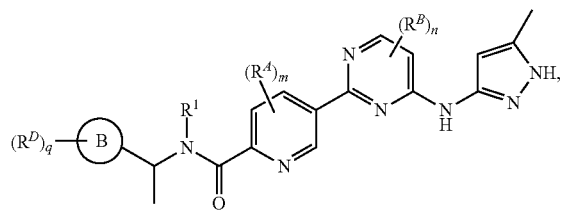

or a pharmaceutically acceptable salt thereof, wherein each of $R^1$, $R^A$, $R^B$, $R^D$, ring B, m, n and q are defined as for Formula I.

In some embodiments, the invention provides a compound of Formula I(d):

I(d)

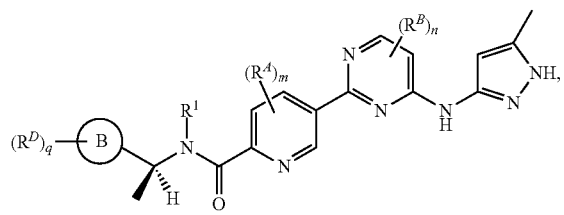

wherein each of $R^1$, $R^A$, $R^B$, $R^D$, ring B, m, n and q are defined as for Formula I.

In some embodiments, the invention provides a compound of Formula I(e):

I(e)

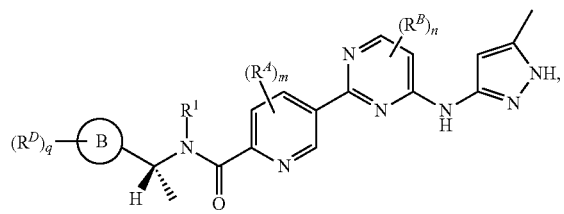

wherein each of $R^1$, $R^A$, $R^B$, $R^D$, ring B, m, n and q are defined as for Formula I.

In some embodiments of Formulae I, I(b), I(c), I(d), or I(e), $R^1$ is hydrogen.

In some embodiments of Formulae I, I(b), I(c), I(d), or I(e), n is 0 or 1. In some aspects of these embodiments, n is 0. In alternate aspects of these embodiments, n is 1. In more specific aspects of these embodiments, n is 1 and $R^B$ is $C_1$-$C_4$ alkyl. In even more specific aspects of these embodiments, n is 1 and $R^B$ is methyl.

In some embodiments of Formulae I, I(b), I(c), I(d), or I(e), m is 0 or 1. In some aspects of these embodiments, m is 0. In alternate aspects of these embodiments, m is 1. In more specific aspects of these embodiments, m is 1 and $R^A$ is $C_1$-$C_4$ alkyl or halo. In even more specific aspects of these embodiments, m is 0, or m is 1 and $R^A$ is methyl or fluoro.

In some embodiments of Formulae I, I(b), I(c), I(d), or I(e), ring B is selected from aryl, heteroaryl and heterocyclyl. In some aspects of these embodiments, ring B is selected from phenyl, furanyl, thiazolyl, pyridinyl, pyrazinyl and isoindolinyl. In more specific aspects of these embodiments, ring B is selected from phenyl, furan-3-yl, thiazol-5-yl, pyridin-2-yl, pyridin-3-yl, pyrazin-2-yl and, when $L^2$ is —C(O)—, isoindolin-1-yl.

In some embodiments of Formulae I, I(b), I(c), I(d), or I(e), q is 0, 1, or 2. In one aspect of these embodiments, q is 0. In another aspect of these embodiments, q is 1 or 2 and each q is independently selected from halo, $C_1$-$C_4$ alkyl, $C_1$-$C_4$ fluoroalkyl, —O—$C_1$-$C_4$ alkyl, —O—$C_1$-$C_4$ fluoroalkyl, and optionally substituted heteroaryl. In more specific aspects of these embodiments, q is 1 or 2 and each q is independently selected from fluoro, chloro, methyl, —O—$CH_3$, —O—$CH_2CH_3$, —O—$CH(CH_3)_2$, —O—$CHF_2$, —O—$CF_3$, and optionally substituted 1H-pyrazol-1-yl. In even more specific aspects of these embodiments, q is 1 or 2 and each q is independently selected from fluoro, chloro, methyl, —O—$CH_3$, —O—$CH_2CH_3$, —O—$CH(CH_3)_2$, —O—$CHF_2$, —O—$CF_3$, 4-methyl-1H-pyrazol-1-yl, 1H-pyrazol-1-yl, 4-fluoro-1H-pyrazol-1-yl, 4-cyano-1H-pyrazol-1-yl, 3,5-dimethyl-1H-pyrazol-1-yl, 3-cyclopropyl-1H-pyrazol-1-yl, 4-cyclopropyl-1H-pyrazol-1-yl, 4-(1-hydroxyethyl)-1H-pyrazol-1-yl, 4-difluoromethyl-1H-pyrazol-1-yl, and 3-methyl-4-difluoromethyl-1H-pyrazol-1-yl.

The table below shows the structures of exemplary compounds of the invention.

| Compound | Structure |
|---|---|
| 1 | 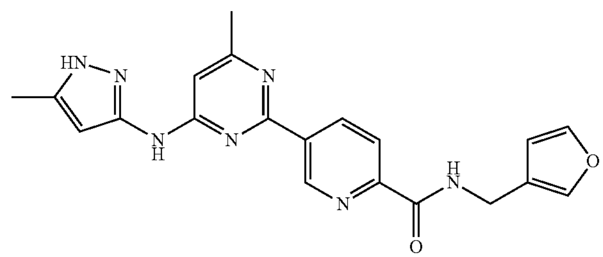 [SMILES: Cc1cc(Nc2cc(C)[nH]n2)nc(-c2ccc(C(=O)NCc3ccoc3)nc2)n1] |
| 2 | 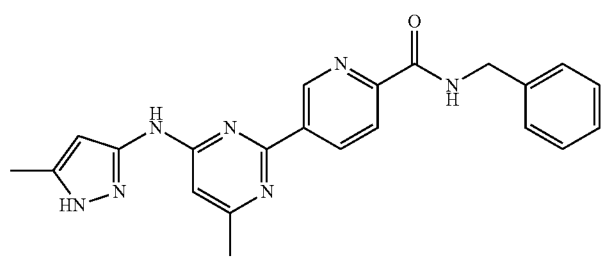 [SMILES: Cc1cc(Nc2cc(C)[nH]n2)nc(-c2ccc(C(=O)NCc3ccccc3)nc2)n1] |
| 3 | 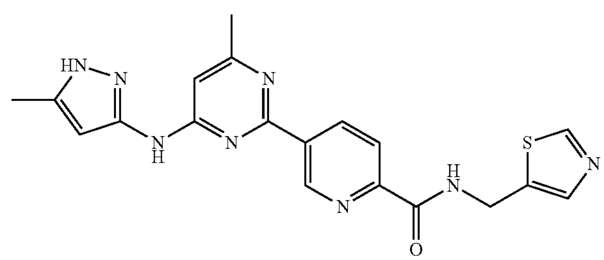 [SMILES: Cc1cc(Nc2cc(C)[nH]n2)nc(-c2ccc(C(=O)NCc3cncs3)nc2)n1] |
| 4 | 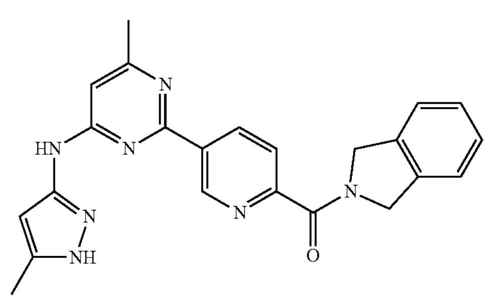 [SMILES: Cc1cc(Nc2cc(C)[nH]n2)nc(-c2ccc(C(=O)N3Cc4ccccc4C3)nc2)n1] |

-continued

| Compound | Structure |
|---|---|
| 5 | 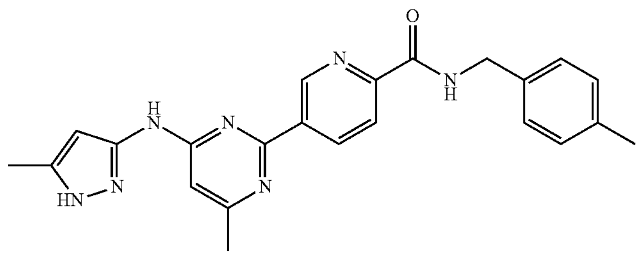 |
| 6 | 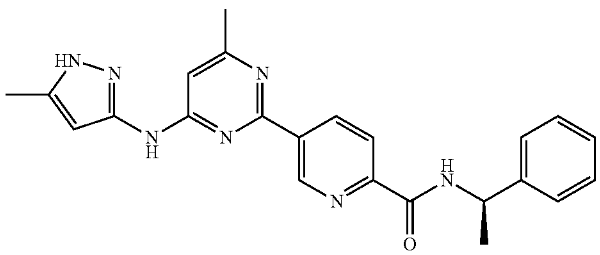 [SMILES: Cc1cc(Nc2cc(C)[nH]n2)nc(-c2ccc(C(=O)N[C@H](C)c3ccccc3)nc2)n1] |
| 7 | 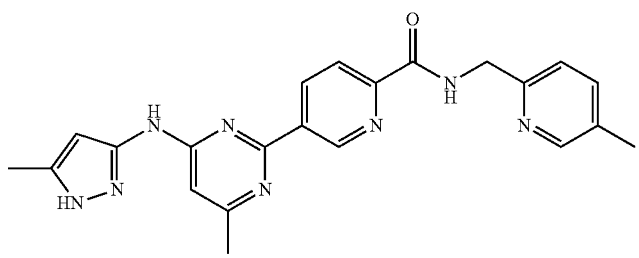 |
| 8 | 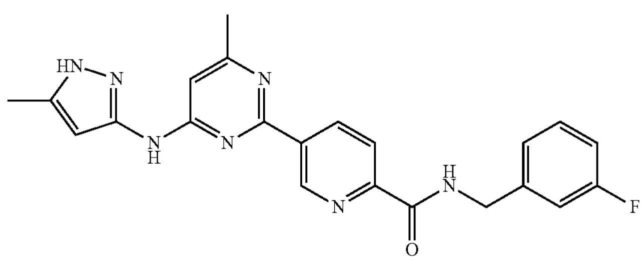 [SMILES: Cc1cc(Nc2cc(C)[nH]n2)nc(-c2ccc(C(=O)NCc3cccc(F)c3)nc2)n1] |
| 9 | 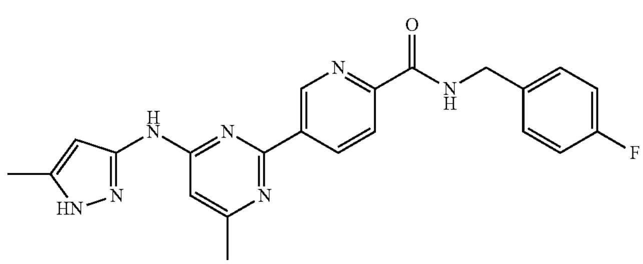 [SMILES: Cc1cc(Nc2cc(C)[nH]n2)nc(-c2ccc(C(=O)NCc3ccc(F)cc3)nc2)n1] |
| 10 | 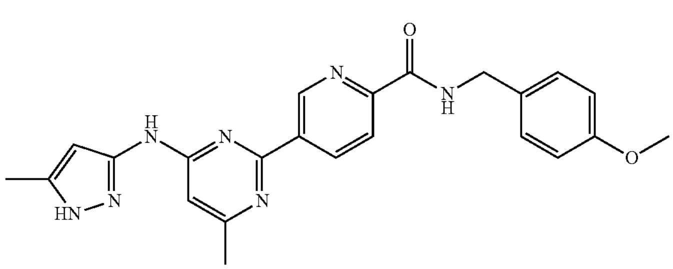 |

-continued

| Compound | Structure |
|---|---|
| 11 | 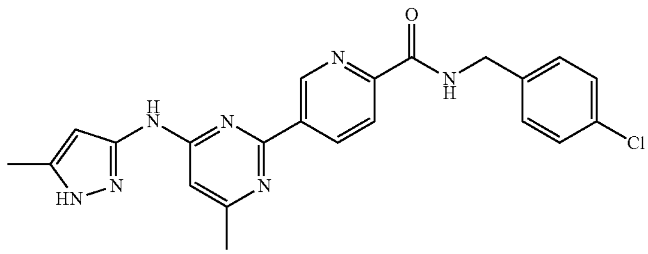 [SMILES: Cc1cc(Nc2cc(C)[nH]n2)nc(-c2ccc(C(=O)NCc3ccc(Cl)cc3)nc2)n1] |
| 12 | 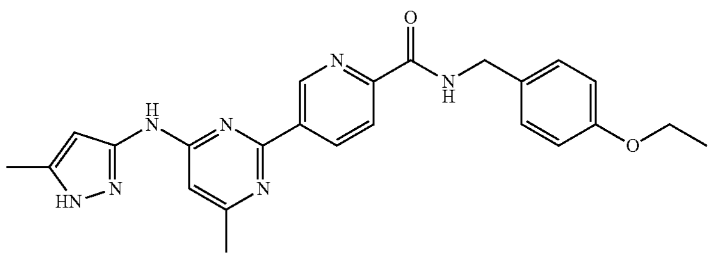 [SMILES: CCOc1ccc(CNC(=O)c2ccc(-c3nc(C)cc(Nc4cc(C)[nH]n4)n3)cn2)cc1] |
| 13 | 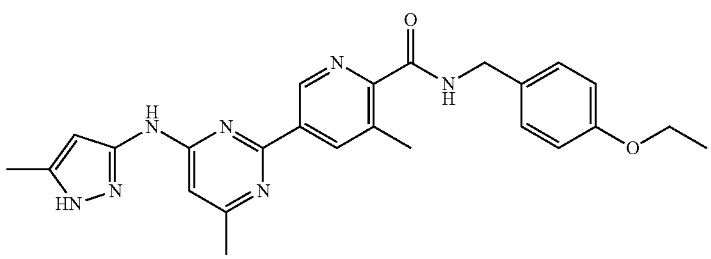 [SMILES: CCOc1ccc(CNC(=O)c2ncc(-c3nc(C)cc(Nc4cc(C)[nH]n4)n3)cc2C)cc1] |
| 14 | 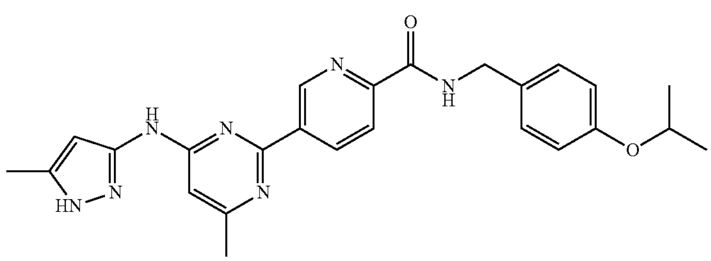 [SMILES: Cc1cc(Nc2cc(C)[nH]n2)nc(-c2ccc(C(=O)NCc3ccc(OC(C)C)cc3)nc2)n1] |
| 15 | 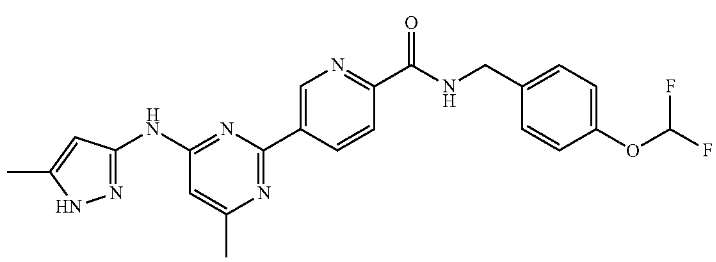 [SMILES: Cc1cc(Nc2cc(C)[nH]n2)nc(-c2ccc(C(=O)NCc3ccc(OC(F)F)cc3)nc2)n1] |
| 16 | 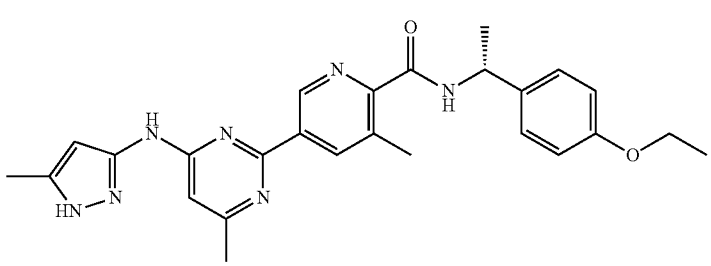 [SMILES: CCOc1ccc([C@@H](C)NC(=O)c2ncc(-c3nc(C)cc(Nc4cc(C)[nH]n4)n3)cc2C)cc1] |

-continued
| Compound | Structure |
|---|---|
| 17 | 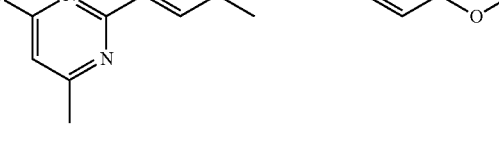 |
| 18 | 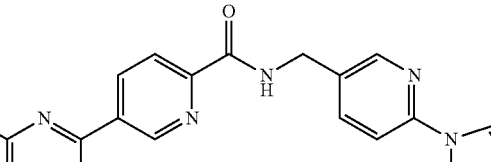 |
| 19 | 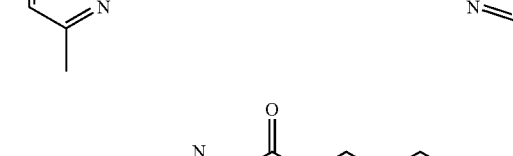 |
| 20 | 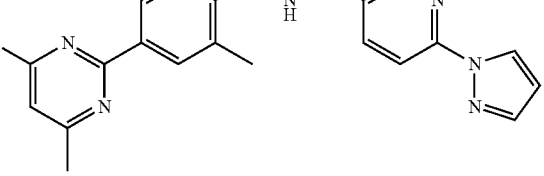 |
| 21 | 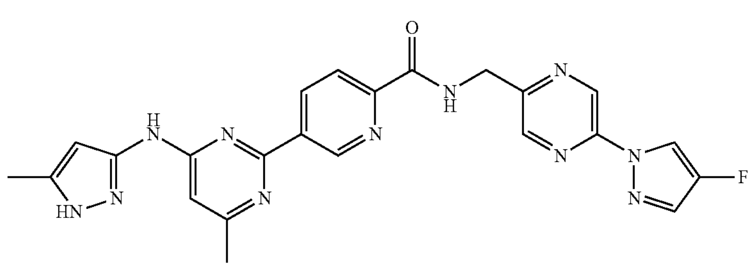 [SMILES: Cc1cc(Nc2cc(C)[nH]n2)nc(-c2ccc(C(=O)NCc3cnc(-n4cc(F)cn4)cn3)nc2)n1] |
| 22 | 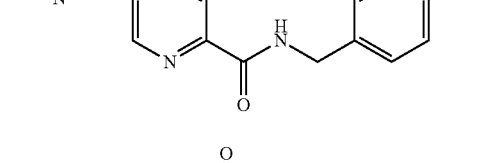 |

| Compound | Structure |
|---|---|
| 23 | (5-(4-((5-methyl-1H-pyrazol-3-yl)amino)-6-methylpyrimidin-2-yl)-3-methyl-N-[(1S)-1-(6-(1H-pyrazol-1-yl)pyridin-3-yl)ethyl]pyridine-2-carboxamide) |
| 24 | (5-(4-((5-methyl-1H-pyrazol-3-yl)amino)-6-methylpyrimidin-2-yl)-N-((6-(3,5-dimethyl-1H-pyrazol-1-yl)pyridin-3-yl)methyl)pyridine-2-carboxamide) |
| 25 | (5-(4-((5-methyl-1H-pyrazol-3-yl)amino)-6-methylpyrimidin-2-yl)-N-[(1S)-1-(6-(4-fluoro-1H-pyrazol-1-yl)pyridin-3-yl)ethyl]pyridine-2-carboxamide) |
| 26 | (5-(4-((5-methyl-1H-pyrazol-3-yl)amino)-6-methylpyrimidin-2-yl)-N-((6-(3-cyclopropyl-1H-pyrazol-1-yl)pyridin-3-yl)methyl)pyridine-2-carboxamide) |
| 27 | (5-(4-((5-methyl-1H-pyrazol-3-yl)amino)-6-methylpyrimidin-2-yl)-N-((6-(4-cyclopropyl-1H-pyrazol-1-yl)pyridin-3-yl)methyl)pyridine-2-carboxamide) |
| 28 | (5-(4-((5-methyl-1H-pyrazol-3-yl)amino)-6-methylpyrimidin-2-yl)-N-((6-(4-(2-hydroxyethyl)-1H-pyrazol-1-yl)pyridin-3-yl)methyl)pyridine-2-carboxamide) |

-continued

| Compound | Structure |
|---|---|
| 29 | 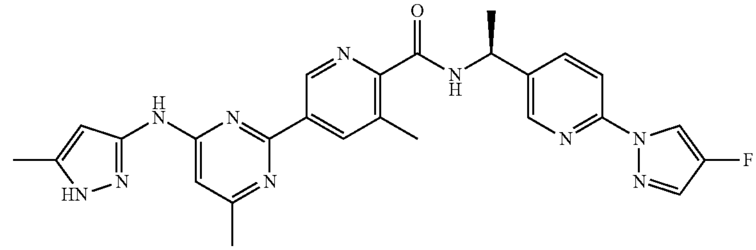 [SMILES: Cc1cc(Nc2cc(C)[nH]n2)nc(-c2cnc(C(=O)N[C@@H](C)c3ccc(-n4cc(F)cn4)nc3)c(C)c2)n1] |
| 30 | 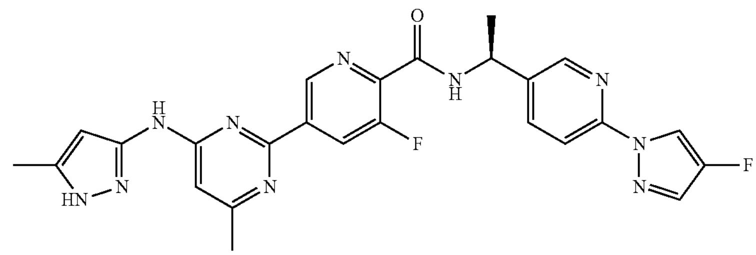 [SMILES: Cc1cc(Nc2cc(C)[nH]n2)nc(-c2cnc(C(=O)N[C@@H](C)c3ccc(-n4cc(F)cn4)nc3)c(F)c2)n1] |
| 31 | 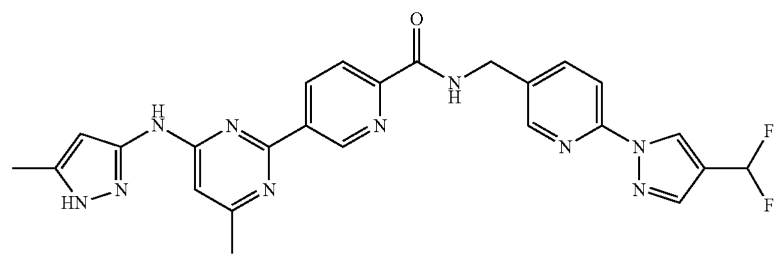 [SMILES: Cc1cc(Nc2cc(C)[nH]n2)nc(-c2ccc(C(=O)NCc3ccc(-n4cc(C(F)F)cn4)nc3)nc2)n1] |
| 32 | 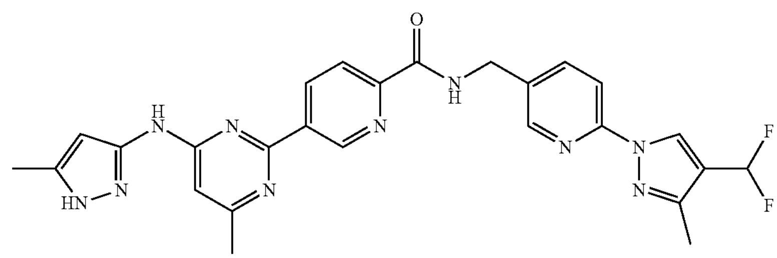 [SMILES: Cc1cc(Nc2cc(C)[nH]n2)nc(-c2ccc(C(=O)NCc3ccc(-n4cc(C(F)F)c(C)n4)nc3)nc2)n1] |
| 33 | 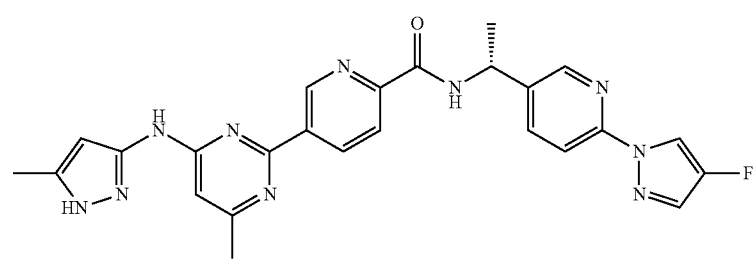 [SMILES: Cc1cc(Nc2cc(C)[nH]n2)nc(-c2ccc(C(=O)N[C@H](C)c3ccc(-n4cc(F)cn4)nc3)nc2)n1] |
| 34 | 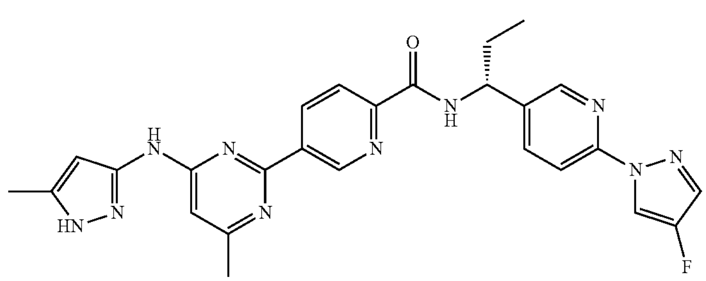 [SMILES: CC[C@@H](NC(=O)c1ccc(-c2nc(C)cc(Nc3cc(C)[nH]n3)n2)cn1)c1ccc(-n2cc(F)cn2)nc1] |

| Compound | Structure |
|---|---|
| 35 | (structure) |

Pharmaceutically acceptable salts of these compounds are also contemplated for the uses described herein.

"Pharmaceutically acceptable salt" refers to any salt of a compound of the invention which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Pharmaceutical Compositions

Pharmaceutical compositions of the invention comprise one or more compounds of the invention and one or more physiologically or pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the invention are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Dosages

Toxicity and therapeutic efficacy of compounds of the invention, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Treatment

RET fusions have been implicated in several types of cancers. Generally, these RET fusions have a RET kinase domain that is the same as in wild-type RET; therefore, as used herein, any RET protein with the same kinase domain as wild-type RET will be referred to as "wild-type RET." Mutations can occur in the RET kinase domain, leading to resistant mutants of RET.

The activity of exemplary compounds that are approved or in development for RET-related conditions is shown below. As shown, the compounds are active against the wild-type RET, but are much less active against the mutated forms.

| Compound | RET wt Biochemical $IC_{50}$ (nM) | RET V804L Biochemical $IC_{50}$ (nM) | RET V804M Biochemical $IC_{50}$ (nM) |
| --- | --- | --- | --- |
| Cabozantinib | 46 | 219 | 585 |
| Vandetanib | 1.2 | 902 | 607 |
| Sorafenib | 7.9 | 95.2 | 32.4 |
| Regorafenib | 5.1 | 29.8 | 46.7 |

The invention provides compounds that inhibit both wild-type RET and resistant mutants of RET. In addition, the compounds of the invention can be selective for wild-type RET, over other kinases, thus leading to reduced toxicities associated with inhibiting other kinases.

In addition, the invention provides inhibitors of mutant RET. Mutations can be predicted using structural biology and computational analyses, as well as by examining codon sequences in which a sequence change gives rise to a codon for a different amino acid. Using such methods, resistant mutants for RET are predicted to have point mutations at the 804 gatekeeper residue in the RET protein and/or at residues at or near the gatekeeper residue. In some embodiments, the mutation may be at one or more of the 804, 806, 810, 865, 870, 891, and 918 residues. Specific examples of RET resistant mutants include: V804L, V804M, V804E, Y806C, Y806S, Y806H, Y806N, G810R, G810S, L865V, L870F, 5891A and M918T mutants.

Mutations occurring from administration of a particular inhibitor (e.g., a known RET wild-type inhibitor) can be determined experimentally by exposing cells to a mutation-promoting agent, such as ENU. The cells are washed, then plated with increasing concentrations (2-100× proliferation $IC_{50}$) of the compound of choice. The wells with cellular outgrowth are then collected after 3-4 weeks. The RET kinase domain is then sequenced to identify resistance mutations (i.e., altered forms of the RET protein that retain enzymatic activity). Resistance can be confirmed by exposing these cells with the compound of choice. Resistant mutants that have been identified experimentally include the V804L, V804E, V804M, and Y806H mutants.

Because of their activity against wild-type RET and mutant RET, the compounds described herein can be used to treat a patient with a condition associated with aberrant RET activity. They can also be used to treat various cancers. In some embodiments, the cancer is selected from papillary thyroid carcinoma (PTC), medullary thyroid cancer (MTC), pheochromocytoma (PC), pancreatic ductal adenocarcinoma, multiple endocrine neoplasia (MEN2A and MEN2B), metastatic breast cancer, testicular cancer, small cell lung cancer, non-small cell lung cancer, chronic myelomonocytic leukemia, colorectal cancer, ovarian cancer, and cancers of the salivary gland.

The compounds can also be used to treat a patient who has developed resistance to a wild-type RET inhibitor, or a patient with a particular RET mutant. The method includes the step of administering a compound or composition of the invention that is active against one or more RET resistant mutants. In certain embodiments, the RET resistant mutant is selected from V804L, V804M, V804E, Y806C, Y806S, Y806N, Y806H, G810R, G810S, L865V, L870F, S891A and M918T. By "active" is meant that a compound has an $IC_{50}$ of less than 1 μM, 500 nM, 250 nM, 100 nM, 75 nM, 50 nM, 25 nM, 10 nM, or 5 nM when measured in a biochemical assay, against at least one resistant mutant.

The compounds and compositions described herein can be administered alone or in combination with other compounds, including other RET-modulating compounds, or other therapeutic agents. In some embodiments, the compound or composition of the invention may be administered in combination with one or more compounds selected from Cabozantinib (COMETRIQ), Vandetanib (CALPRESA), Sorafenib (NEXAVAR), Sunitinib (SUTENT), Regorafenib (STAVARGA), Ponatinib (ICLUSIG), Bevacizumab (AVASTIN), Crizotinib (XALKORI), or Gefitinib (IRESSA). The compound or composition of the invention may be administered simultaneously or sequentially with the other therapeutic agent by the same of different routes of administration. The compound of the invention may be included in a single formulation with the other therapeutic agent or in separate formulations.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC).Analytical instruments and methods for compound characterization:

LC-MS:

Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS:

Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica Gel Chromatography:

Silica gel chromatography was performed on either a Teledyne Isco CombiFlash® Rf unit or a Biotage® Isolera Four unit.

Proton NMR:

Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d$^6$ solvent as parts-per million (ppm) with respect to residual DMSO (2.50 ppm).

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Protocol 1

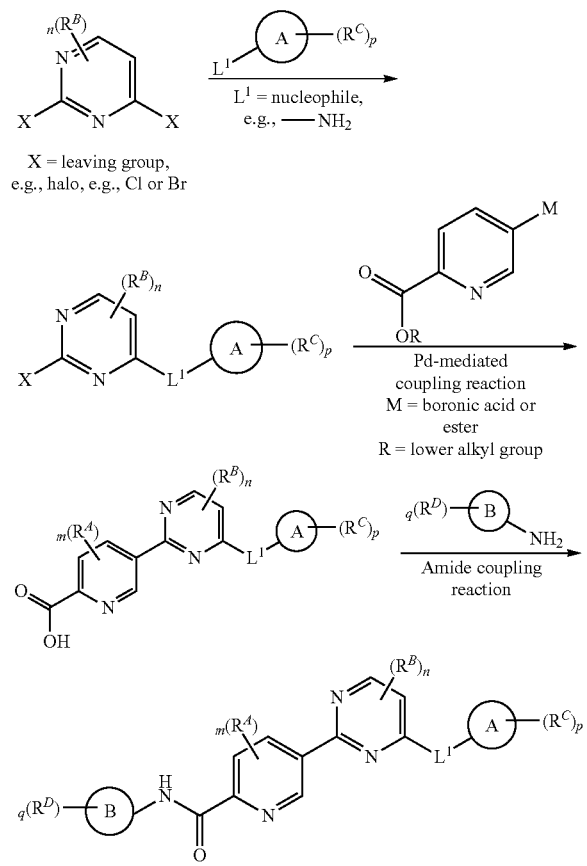

The pyrimidine can be coupled to Ring A under nucleophilic aromatic substitution reaction conditions using a base such as diisopropylethylamine (DIPEA) or triethylamine (TEA) in a polar solvent to provide the bicyclic ring system. The pyrimidine of the bicyclic ring system can be coupled to a boron, tin or zinc aryl or heteroaryl reagent via a Palladium-mediated coupling reaction, e.g., Suzuki, Stille, Negishi coupling, to provide the tricyclic ring system. For example, in Synthetic Protocol 1, the pyrimidine ring of the bicyclic ring system can be coupled to the ester substituted pyridine under Suzuki coupling reaction conditions (X=halo, e.g., chloro; and M=B(OR)$_2$) to provide the tricyclic carboxylic acid intermediate. The carboxylic acid can be coupled to a variety of amines, such as those described below under the heading "Synthesis of Amine Intermediates," to provide the amide final product.

Example 1. General Synthesis of Compound 25 and Related Analogs

Step 1: Synthesis of 2-chloro-6-methyl-N-(5-methyl-1H-pyrazol-3-yl)pyrimidin-4-amine A suspension of 2,4-dichloro-6-methyl-pyrimidine (120.00 g, 736.2 mmol, 1.00 eq), 5-methyl-1H-pyrazol-3-amine (78.65 g, 0.81 mol, 1.10 eq) and DIPEA (142.72 g, 1.10 mol, 1.50 eq) in DMSO (400.00 mL) was heated at 60° C. for 16 hrs. TLC (PE/EA, 5:1, 1:1) showed the reaction was complete. The reaction mixture was cooled to 30° C. and poured into ice-water (800 mL). The resulting mixture was extracted with MTBE (800 mL×10). The combined organic layers were washed with water (400 mL×3), brine (400 mL×3) and dried over Na$_2$SO$_4$. After filtration, the filtrate was concentrated under reduced pressure and the residue was recrystallized from DCM (10 mL/g) to afford 2-chloro-6-methyl-N-(5-methyl-1H-pyrazol-3-yl)pyrimidin-4-amine (105.60 g, 472.14 mmol, 64%) as a yellow solid. The structure was confirmed by LC-MS and NMR.

Step 2: Synthesis of 5-(4-methyl-6-((5-methyl-1H-pyrazol-3-yl)amino)pyrimidin-2-yl)picolinic acid 2-chloro-6-methyl-N-(5-methyl-1H-pyrazol-3-yl)pyrimidin-4-amine (2.05 g, 9.17 mmol) (6 (methoxycarbonyl) pyridin-3-yl)boronic acid (2.65 g, 1.6 eq), and Pd(PPh3)4 (0.5 g, 0.05 eq) and sodium carbonate (1.94 g, 2 eq) were suspended in a mixture of ethanol (22.9 mL) toluene (11.5 mL) and water (11.5 mL) in a sealed tube. The tube was capped and heated with stirring 135° C. overnight. LC-MS showed the reaction was about 60-70% complete. LC-MS showed unreacted chloropyrimidine in addition to desired product. An additional 2.4 g of) (6 (methoxycarbonyl) pyridin-3-yl)boronic acid, 530 mg of Pd(PPh3)4, and 1.9 g of sodium carbonate were added. The reaction mixture was stirred overnight at 135° C. after degassing with nitrogen. After heating an additional 14 hours at 135-140° C. LC-MS showed at least 90% conversion to the desired product, 100% hydrolyzed to the carboxylic acid. The reaction was treated with water (~15 mL and 3×10 mL washes), and a light orange solid was removed by filtration. The filtrate was concentrated down to ½ volume, and extracted with EtOAc (~15 mL). The layers were separated, and the aqueous layer was carefully acidified to pH 4.5-5 with concentrated HCl. A fine, light orange solid was slowly isolated by filtration (overnight). The wet cake was washed with water (2×5 mL). After most of the water had been filtered off, the wet cake was dissolved into 500 mL of 1:1 MeOH/DCM. The mixture was sonicated until all the product was dissolved. The solution was dried over 5-6 g of magnesium sulfate, which was then removed by filtration. The filtrate was concentrated down and dried to yield 1.729 g of yellow/light orange solid. LC-MS confirmed desired product in 90-95% purity.

Step 3: Synthesis of (S)—N-(1-(6-(4-fluoro-1H-pyrazol-1-yl)pyridin-3-yl)ethyl)-5-(4-methyl-6-((5-methyl-1H-pyrazol-3-yl)amino)pyrimidin-2-yl)picolinamide 5-(4-Methyl-6-((5-methyl-1H-pyrazol-3-yl)amino)pyrimidin-2-yl)picolinic acid (299 mg, 0.942 mmol) and (S)-1-(6-(4-fluoro-1H-pyrazol-1-yl)pyridin-3-yl)ethan-1-amine (315 mg, 1.13 mmol) were dissolved in DMF (4.7 mL). Diisopropylethylamine (1 mL, 0.73 g, 5.7 mmol) was added followed by HATU (430 mg, 1.13 mmol). At 30 minutes, LC-MS showed the reaction was complete. The reaction was treated with 5N NaOH/water (20 mL), sonicated, and stirred. A light orange solid was isolated by filtration. The crude was eluted on a 40 gram silica gel column with a DCM to 15% MeOH/DCM gradient over 45 minutes. The desired peak eluted at around 5-9% MeOH/DCM. The fractions containing nearly pure desired product were combined, concentrated down, and dried. This solid (~320 mg) was treated with dichloromethane (~2 mL). A light yellow solid was isolated by filtration, washed with small amounts of DCM, and dried to yield (S)—N-(1-(6-(4-fluoro-1H-pyrazol-1-yl)pyridin-3-yl)ethyl)-5-(4-methyl-6-((5-methyl-1H-pyrazol-3-yl)amino)pyrimidin-2-yl)picolinamide (249.1 mg, 50.9% yield). MS: M+1=499.2.

Synthetic Protocol 2

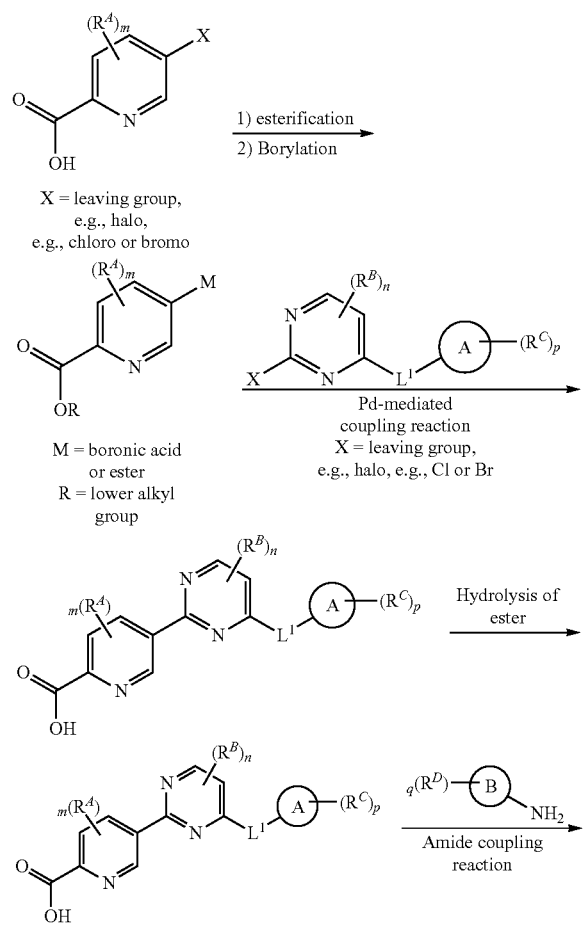

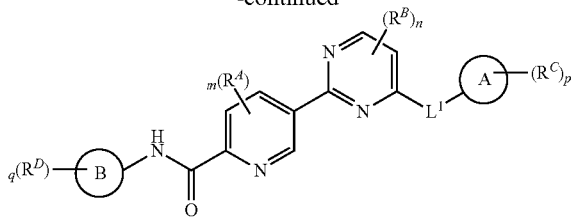

The substituted pyridine can be esterified using known methods in the art followed by conversion to the organometallic intermediate (wherein M=metal, e.g., boronic acid). The organometallic intermediate can be coupled to the substituted pyrimidine under Palladium-mediated coupling conditions, e.g., Suzuki, Stille, Negishi coupling, to provide the tricyclic ring system. Upon hydrolysis of the ester, the resultant carboxylic acid can be reacted with an amine, such as an amine as described below under the heading "Synthesis of Amine Intermediates," using amide coupling reaction conditions (such as HATU and diisopropylethylamine) to provide the final compound. Compound 29 in Example 2 (below) and related analogs were prepared by the methods described above in Synthetic Protocol 2.

Example 2. General Synthesis of Compound 29 and Related Analogs

Step 1: Synthesis of methyl 5-bromo-3-methylpicolinate

To a mixture of 5-bromo-3-methylpicolinic acid (600 mg, 2.8 mmol) in MeOH (10 mL) was added $SOCl_2$ (397 mg, 3.3 mmol). The mixture was stirred at reflux temperature for 6 hours. LCMS showed the reaction was complete. The reaction mixture was evaporated in vacuo to afford methyl 5-bromo-3-methylpicolinate (640 mg, 99% yield), m/z=229.76 $(M+H)^+$, as an off-white solid.

Step 2: Synthesis of (6-(methoxycarbonyl)-5-methylpyridin-3-yl)boronic acid A mixture of methyl 5-bromo-3-methylpicolinate (640 mg, 2.78 mmol), bis(pinacolato)diboron (1.06 g, 4.17 mmol), KOAc (681 mg, 6.96 mmol) and $Pd(dppf)Cl_2$ (102 mg, 0.14 mmol) in 1, 4-dioxane (8 mL) was stirred under $N_2$ at 100° C. for 4 hours. LCMS showed the reaction was fully converted to (6-(methoxycarbonyl)-5-methylpyridin-3-yl) boronic acid. The crude product was used in the next step directly without any purification. m/z=195.80 $(M+H)^+$.

Step 3: Synthesis of 3-methyl-5-(4-methyl-6-((5-methyl-1H-pyrazol-3-yl)amino)pyrimidin-2-yl)picolinate A mixture of 2-chloro-6-methyl-N-(5-methyl-1H-pyrazol-3-yl)pyrimidin-4-amine (500 mg, 2.23 mmol), (6-(methoxycarbonyl)-5-methylpyridin-3-yl)boronic acid (crude), $Cs_2CO_3$ (1.46 g, 4.46 mmol) and $Pd(dppf)Cl_2$ (163 mg, 0.22 mmol) in 1, 4-dioxane/$H_2O$ (10 mL/1 mL) was stirred under $N_2$ at 110° C. for 16 hours. LCMS showed the reaction was complete. Then the mixture was filtered and the filtrate was purified by prep-TLC (ethyl acetate) to afford methyl 3-methyl-5-(4-methyl-6-((5-methyl-1H-pyrazol-3- yl)amino)pyrimidin-2-yl)picolinate (300 mg, 40% yield), m/z=338.96 (M+H)⁺, as a yellow solid.

Step 4: Synthesis of 3-methyl-5-(4-methyl-6-((5-methyl-1H-pyrazol-3-yl)amino)pyrimidin-2-yl)picolinic acid A mixture of methyl 3-methyl-5-(4-methyl-6-((5-methyl-1H-pyrazol-3-yl)amino)pyrimidin-2-yl)picolinate (300 mg, 0.89 mmol) in MeOH/H$_2$O (3 mL/3 mL) was added lithium hydroxide (106 mg, 4.4 mmol). The mixture was stirred at room temperature for 16 hours. Then MeOH was removed in vacuo and water (5 mL) was added. HCl (6 M) was added to adjust the reaction mixture to a pH of approximately 3. The solid in the mixture was separated and dried to afford 3-methyl-5-(4-methyl-6-((5-methyl-1H-pyrazol-3-yl)amino)pyrimidin-2-yl)picolinic acid (120 mg, 41% yield), m/z=325.02 (M+H)⁺, as a yellow solid.

Step 5: Synthesis of (S)—N-(1-(6-(4-fluoro-1H-pyrazol-1-yl)pyridin-3-yl)ethyl)-3-methyl-5-(4-methyl-6-((5-methyl-1H-pyrazol-3-yl)amino)pyrimidin-2-yl)picolinamide A mixture of 3-methyl-5-(4-methyl-6-((5-methyl-1H-pyrazol-3-yl)amino)pyrimidin-2-yl)picolinic acid (30 mg, 0.09 mmol), (S)-1-(6-(4-fluoro-1H-pyrazol-1-yl)pyridin-3-yl)ethan-1-amine (0.12 mmol), DIEA (36 mg, 0.28 mmol) and HATU (42 mg, 0.11 mmol) in DMF (1 mL) was stirred at room temperature for 2 hours. The resulting mixture was purified by prep-HPLC to give the target compound. (18 mg).

Synthetic Protocol 3

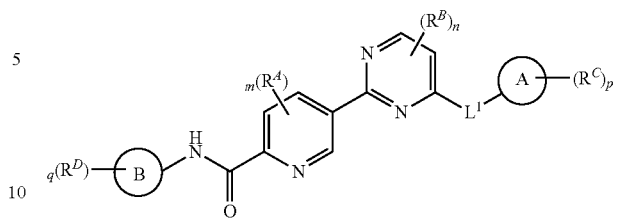

The carboxylic acid substituted pyridine can be reacted with an amine, such as those described below under the heading "Synthesis of Amine Intermediates," using amide coupling reaction conditions (such as HATU and diisopropylethylamine) to provide the bicyclic amide. The bicyclic amide can be converted to the organometallic intermediate and then coupled to the substituted pyrimidine under Palladium-mediated coupling conditions, e.g., Suzuki, Stille, Negishi coupling, to provide the tricyclic ring system.

Example 3: Synthesis of (S)-3-fluoro N (1 (6 (4 fluoro-1H-pyrazol-1-yl)pyridin-3-yl)ethyl)-5-(4-methyl-6-((5-methyl-1H-pyrazol-3-yl)amino)pyrimidin-2-yl)picolinamide (Compound 30)

Synthesis of (S)-3-fluoro-N-(1-(6-(4-fluoro-1H-pyrazol-1-yl)pyridin-3-yl)ethyl)-5-(4,4,5,5-tetramethyl-1,3,2-dioxaborolan-2-yl)picolinamide

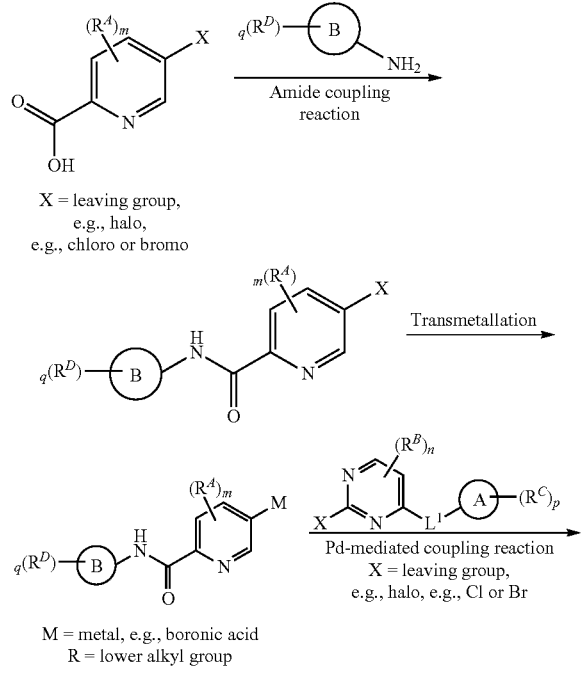

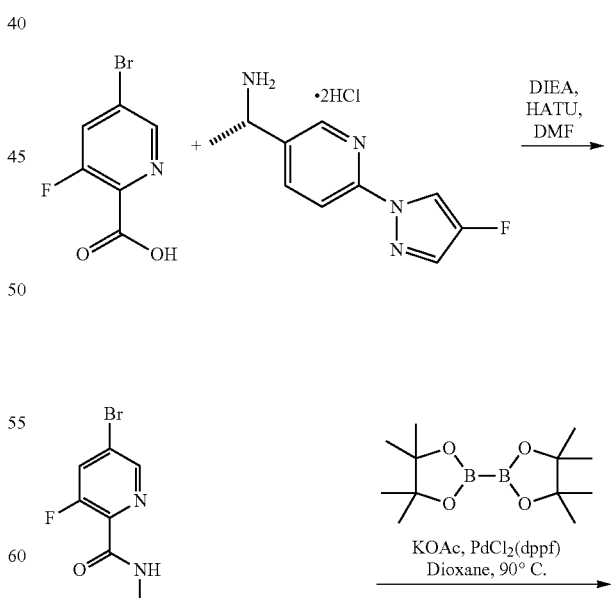

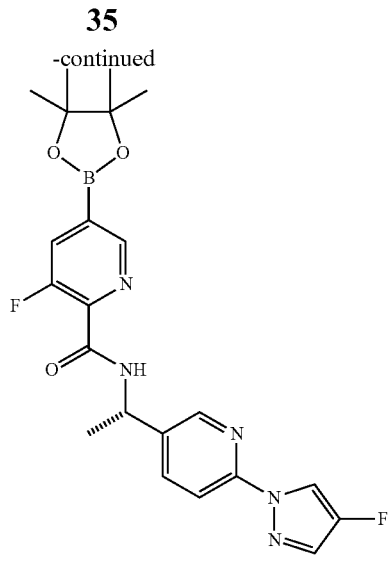

Step 1: Synthesis of (S)-5-bromo-3-fluoro-N-(1-(6-(4-fluoro-1H-pyrazol-1-yl)pyridin-3-yl)ethyl)picolinamide A mixture of (S)-1-(6-(4-fluoro-1H-pyrazol-1-yl)pyridin-3-yl)ethanamine (340 mg, 1.21 mmol) and 5-bromo-3-fluoropicolinic acid (255 mg, 1.16 mmol) in diisopropylethylamine (1.2 mL, 900 mg, 7.0 mmol) and N,N-dimethylformamide (2.9 mL) was stirred and sonicated to a near solution before addition of HATU (530 mg, 1.39 mmol). After 5 minutes, the reaction was treated with 5N aqueous NaOH (20 mL), sonicated, and stirred for 20 minutes. A light yellow, sticky solid was isolated by filtration, dried, and loaded onto a 24 g silica gel column, which was eluted with a DCM to 10% MeOH/DCM gradient over 45 minutes. The test tubes containing pure desired product by TLC were combined, concentrated down, and dried to yield (S)-5-bromo-3-fluoro-N-(1-(6-(4-fluoro-1H-pyrazol-1-yl)pyridin-3-yl)ethyl)picolinamide (164 mg, 34.6% yield) as a white solid. MS: M+1=408.0.

Step 2: Synthesis of (S)-3-fluoro-N-(1-(6-(4-fluoro-1H-pyrazol-1-yl)pyridin-3-yl)ethyl)-5-(4,4,5,5-tetramethyl-1,3,2-dioxaborolan-2-yl)picolinamide A mixture of (S)-5-bromo-3-fluoro-N-(1-(6-(4-fluoro-1H-pyrazol-1-yl)pyridin-3-yl)ethyl)picolinamide (164 mg, 0.402 mmol), bis(pinacolato)diboron (112 mg, 0.442 mmol), potassium acetate (118 mg, 1.21 mmol), and PdCl$_2$(dppf) (14.7 mg, 0.020 mmol) in dioxane (1.8 mL) was degassed with nitrogen in a sealed tube, which was then sealed. The mixture was stirred at 90° C. for 1.5 hours. The reaction turned dark red and was nearly a solution. The reaction was cooled to room temperature, diluted with ethyl acetate (250 mL), and washed with brine (200 mL). The organic layer was dried over sodium sulfate, filtered, concentrated down, and dried to yield (S)-3-fluoro-N-(1-(6-(4-fluoro-1H-pyrazol-1-yl)pyridin-3-yl)ethyl)-5-(4,4,5,5-tetramethyl-1,3,2-dioxaborolan-2-yl)picolinamide (280 mg, 65% purity, assumed 100% yield) as a crude, brown thick oil. MS: M+1 (hydrolysis of boronate to boronic acid)=374.1.

Step 3: Synthesis of (S)-3-fluoro-N-(1-(6-(4-fluoro-1H-pyrazol-1-yl)pyridin-3-yl)ethyl)-5-(4-methyl-6-((5-methyl-1H-pyrazol-3-yl)amino)pyrimidin-2-yl)picolinamide A mixture of 2-chloro-6-methyl-N-(5-methyl-1H-pyrazol-3-yl)pyrimidin-4-amine (85 mg, 0.38 mmol), (S)-3-fluoro-N-(1-(6-(4-fluoro-1H-pyrazol-1-yl)pyridin-3-yl)ethyl)-5-(4,4,5,5-tetramethyl-1,3,2-dioxaborolan-2-yl)picolinamide (279 mg, 0.399 mmol), potassium carbonate (158 mg, 1.14 mmol), and tetrakis(triphenylphosphine)palladium(0) (22 mg, 0.019 mmol) in 1,2-dimethoxyethane (2.5 mL) and water (1.3 mL) was degassed with nitrogen in a sealed tube, which was then sealed and stirred at 125° C. for 1.5 hours. The reaction was cooled to room temperature and treated with water (~15 mL). A beige solid was isolated by filtration, dried, and purified by silica gel chromatography to yield (S)-3-fluoro-N-(1-(6-(4-fluoro-1H-pyrazol-1-yl)pyridin-3-yl)ethyl)-5-(4-methyl-6-((5-methyl-1H-pyrazol-3-yl)amino)pyrimidin-2-yl)picolinamide (59.5 mg, 95% purity, 28.8% yield) as a yellow, foamy solid. MS: M+1=517.3.

Synthesis of Amine Intermediates

Synthesis of (S)-1-(6-(4-fluoro-1H-pyrazol-1-yl)pyridin-3-yl)ethan-1-amine

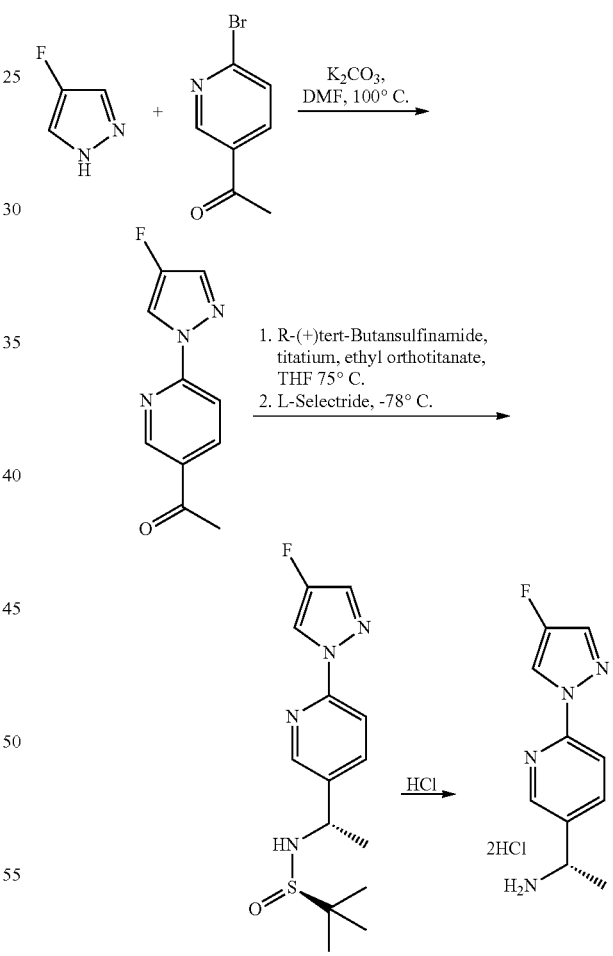

1-(6-(4-fluoro-1H-pyrazol-1-yl)pyridin-3-yl)ethan-1-one

4-Fluoro-1H-pyrazole (4.73 g, 55 mmol) and potassium carbonate (17.27 g, 125 mmol) were combined and stirred in N,N-dimethylformamide (41.7 mL) for 10 minutes in an open sealed tube before addition of 2-bromo-5-acetylpyridine (10 g, 50 mmol). The reaction tube was sealed and stirred 20 hours at 100° C. The reaction mixture was then cooled to room temperature and poured into water (~700 mL). The mixture was sonicated and stirred for 20 minutes. A beige solid was isolated by filtration, washed with small amounts of water, and dried to yield 1-(6-(4-fluoro-1H-pyrazol-1-yl)pyridin-3-yl)ethan-1-one (9.81 g, 96% yield). MS: M+1=206.0.

(R)—N—((S)-1-(6-(4-fluoro-1H-pyrazol-1-yl)pyridin-3-yl)ethyl)-2-methylpropane-2-sulfinamide To a stirred room temperature solution of 1-(6-(4-fluoro-1H-pyrazol-1-yl)pyridin-3-yl)ethan-1-one (9.806 g, 47.8 mmol) in THF (96 mL) was added (R)-(–)-t-Butylsulfinamide (5.79 g, 47.8 mmol) followed by titanium (IV) ethoxide (21.8 g, 96 mmol). The solution was stirred at 75° C. on an oil bath for 15 hours. The reaction solution was cooled to room temperature and then to –78° C. (external temperature) before the next step. To the –78° C. solution was added dropwise over nearly 55 minutes L-Selectride (143 mL of 1N in THF, 143 mmol). During addition, some bubbling was observed. The reaction was then stirred after the addition was completed for 15 minutes at –78° C. before warming to room temperature. LC-MS of sample taken during removal from cold bath showed reaction was completed. The reaction was cooled to –50° C. and quenched slowly with methanol (~10 mL), then poured into water (600 mL) and stirred. An off-white precipitate was removed by filtration, with ethyl acetate used for washes. The filtrate was diluted with ethyl acetate (800 mL), the layers were separated, and the organic layer was dried over sodium sulfate, filtered, and concentrated down. The crude was purified by silica gel chromatography to yield (R)—N—((S)-1-(6-(4-fluoro-1H-pyrazol-1-yl)pyridin-3-yl)ethyl)-2-methylpropane-2-sulfinamide (10.5 g, 99% purity, 70.3% yield) as a light yellow solid. MS: M+1=311.1.

(S)-1-(6-(4-fluoro-1H-pyrazol-1-yl)pyridin-3-yl)ethan-1-amine

A solution of (R)—N—((S)-1-(6-(4-fluoro-1H-pyrazol-1-yl)pyridin-3-yl)ethyl)-2-methylpropane-2-sulfinamide (10.53 g, 33.9 mmol)) in methanol (79 mmol) and 4N HCl/dioxane (85 mL, 339 mmol) was stirred 2.5 hours. LC-MS showed reaction was completed. The reaction solution was poured into diethyl ether (300 mL). A sticky solid was formed. The mixture was treated with ethyl acetate (200 mL) and sonicated. The solvents were decanted, and the sticky solid was treated with more ethyl acetate (~200 mL), sonicated and stirred. The bulk of the sticky solid was converted to a suspension. A light yellow solid was isolated by filtration, washed with smaller amounts of ethyl acetate, and dried to yield (S)-1-(6-(4-fluoro-1H-pyrazol-1-yl)pyridin-3-yl)ethan-1-amine (7.419 g, 78% yield), assumed to be the di-HCl salt. LC-MS confirmed desired product in high purity. MS: M+1=207.1.

Synthesis of (6-(3-cyclopropyl-1H-pyrazol-1-yl)pyridin-3-yl)methanamine

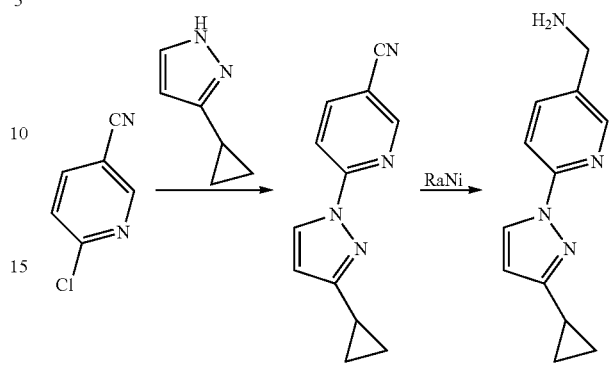

6-(3-cyclopropyl-1H-pyrazol-1-yl)nicotinonitrile

To a solution of 6-chloronicotinonitrile (100 mg, 0.74 mmol) in DMF (2 mL), was added 3-cyclopropyl-1H-pyrazole (80 mg, 0.74 mmol), and Cs₂CO₃ (470 mg, 1.48 mmol). The mixture was stirred at 90° C. for 5 hours. To the mixture was added water and extracted with ethyl acetate. The organic layer was dried with anhydrous Na₂SO₄, and concentrated under vacuo to give 120 mg of 6-(3-cyclopropyl-1H-pyrazol-1-yl)nicotinonitrile as a light yellow solid. The structure was confirmed by LC-MS.

(6-(3-cyclopropyl-1H-pyrazol-1-yl)pyridin-3-yl)methanamine

To a solution of 6-(3-cyclopropyl-1H-pyrazol-1-yl)nicotinonitrile (120 mg, 0.57 mmol) in MeOH (5 mL), was added Raney-Ni (80 mg), NH₃/H₂O (0.2 mL). The mixture was stirred at 25° C. under an atmosphere of hydrogen for 1 hour. The mixture was filtered and concentrated under vacuo to give 100 mg of (6-(3-cyclopropyl-1H-pyrazol-1-yl)pyridin-3-yl)methanamine. The structure was confirmed by LC-MS.

Synthesis of (6-(4-(difluoromethyl)-1H-pyrazol-1-yl)pyridin-3-yl)methanamine

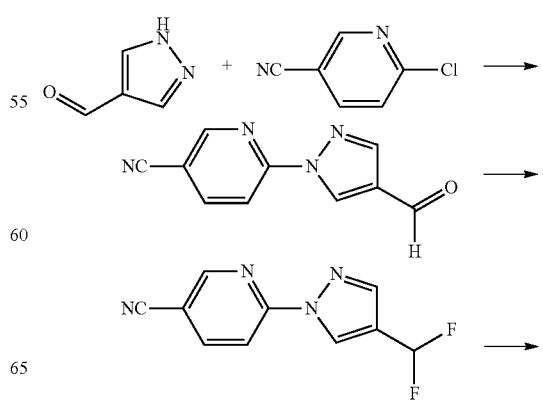

6-(4-formyl-1H-pyrazol-1-yl)nicotinonitrile

To a solution of 1H-pyrazole-4-carbaldehyde (500 mg, 5 mmol) and 6-chloronicotinonitrile (700 mg, 5 mmol) in 20 mL DMSO was added KOAc (2.1 g, 15 mmol). The resulting mixture was stirred at 100° C. for 2 hours. The resulting mixture was concentrated and the crude product was purified by flash column chromatography to give the 6-(4-formyl-1H-pyrazol-1-yl)nicotinonitrile (1.0 g). The structure was confirmed by LC-MS

6-(4-(difluoromethyl)-1H-pyrazol-1-yl)nicotinonitrile

To a solution of 6-(4-formyl-1H-pyrazol-1-yl)nicotinonitrile (300 mg, 1.52 mmol) in 50 mL DCM was added DAST (1.2 g, 7.6 mmol) at −78° C., and the mixture was warmed to RT overnight. Then sat. NaHCO3 was added to mixture until PH=7, washed with water for 3 times. Organic phase was separated and dried over $Na_2SO_4$, purified by flash column to give 6-(4-(difluoromethyl)-1H-pyrazol-1-yl)nicotinonitrile (250 mg). The structure was confirmed by LC-MS.

(6-(4-(difluoromethyl)-1H-pyrazol-1-yl)pyridin-3-yl)methanamine

To a solution of 6-(4-(difluoromethyl)-1H-pyrazol-1-yl)nicotinonitrile (300 mg, 1.36 mmol) in 10 mL of MeOH and 1 mL NH3.H2O was added Raney Ni (50 mg). The reaction mixture was stirred at room temperature for 3 hours under an atmosphere of hydrogen. The resulting mixture was filtered and concentrated to give crude (6-(4-(difluoromethyl)-1H-pyrazol-1-yl)pyridin-3-yl)methanamine which was directly used in the next step. The structure was confirmed by LC-MS.

Synthesis of (6-(4-cyclopropyl-1H-pyrazol-1-yl)pyridin-3-yl)methanamine

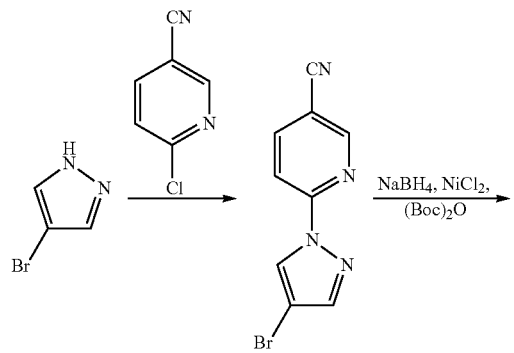

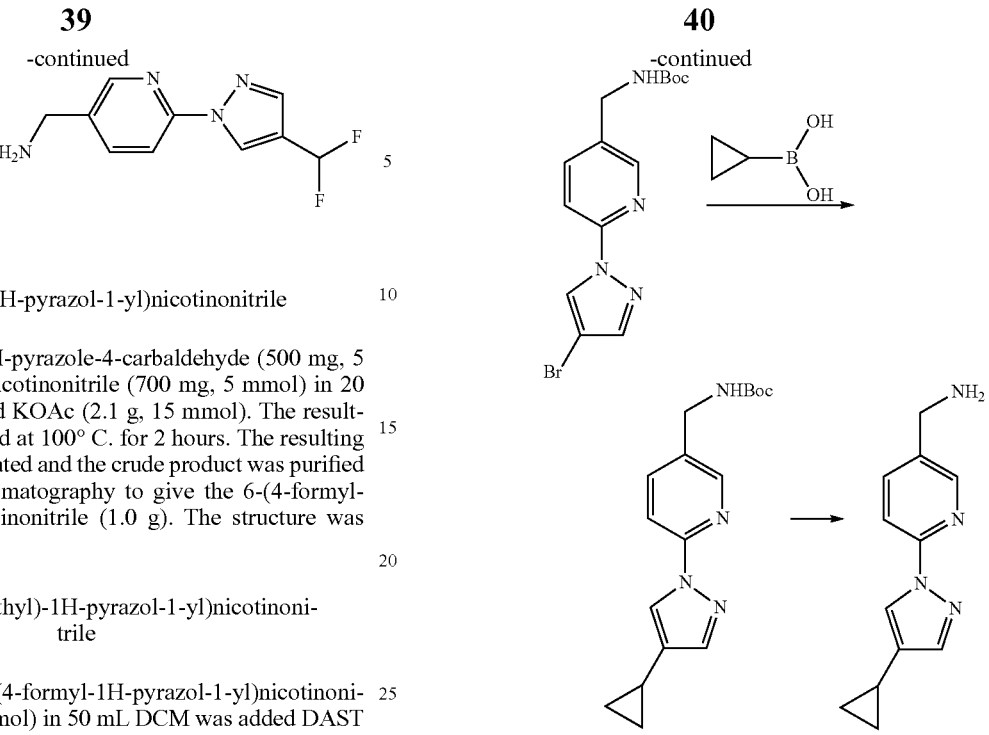

6-(4-bromo-1H-pyrazol-1-yl)nicotinonitrile

To a solution of 4-bromo-1H-pyrazole (100 mg, 0.72 mmol) in DMF (3 mL), was added 6-chloronicotinonitrile (49 mg, 0.72 mmol), and $Cs_2CO_3$ (468 mg, 1.44 mmol). The mixture was stirred at 80° C. for 12 h. The mixture was added water and extracted with EA. The organic layer was dried with anhydrous $Na_2SO_4$, and concentrated under vacuum to give 120 mg of 6-(4-bromo-1H-pyrazol-1-yl)nicotinonitrile as a light yellow solid. The structure was confirmed by LC-MS.

tert-butyl ((6-(4-bromo-1H-pyrazol-1-yl)pyridin-3-yl)methyl)carbamate

To a solution of 6-(4-bromo-1H-pyrazol-1-yl)nicotinonitrile (100 mg, 0.4 mmol) in MeOH (10 mL), was added $(Boc)_2O$ (175 mg, 0.8 mmol) and $NiCl_2$ (26 mg, 0.2 mmol), and then added $NaBH_4$ (38 mg, 1.0 mmol) slowly at 0° C. The mixture was stirred at 25° C. for 1 h. The mixture was added 2 mL of water, and extracted with EA twice. The organic layer was concentrated under vacuum to give 80 mg of tert-butyl ((6-(4-bromo-1H-pyrazol-1-yl)pyridin-3-yl)methyl)carbamate. The structure was confirmed by LC-MS.

tert-butyl ((6-(4-cyclopropyl-1H-pyrazol-1-yl)pyridin-3-yl)methyl)carbamate

A solution of tert-butyl ((6-(4-bromo-1H-pyrazol-1-yl)pyridin-3-yl)methyl)carbamate (380 mg, 1.3 mmol), cyclopropylboronic acid (172 mg, 2.0 mmol), Pd2(dpa)3 (119 mg, 0.13 mmol), Xanthpos (150 mg, 0.26 mmol) and $K_3PO_4$ (828 mg, 3.9 mmol) in toluene (20 mL) was stirred at 100° C. overnight under a nitrogen atmosphere. LC-MS showed the reaction was complete. The solvent was removed by reduce pressure. The mixture was extracted with ethyl acetate (50 mL) twice. The organic solvent was dried with anhydrous $Na_2SO_4$. The crude compound was purified by column chromatograph (DCM:MeOH=100:1) to give tert-butyl ((6-(4-cyclopropyl-1H-pyrazol-1-yl)pyridin-3-yl)methyl)carbamate (280 mg). The structure was confirmed by LC-MS.

(6-(4-cyclopropyl-1H-pyrazol-1-yl)pyridin-3-yl)methanamine

A solution of tert-butyl ((6-(4-cyclopropyl-1H-pyrazol-1-yl)pyridin-3-yl)methyl)carbamate (280 mg, 0.89 mmol) in Dioxane/HCl (6 mL) was stirred at room temperature for two hours. The LC-MS showed that the reaction was complete. The solvent was removed by reduce pressure to give (6-(4-cyclopropyl-1H-pyrazol-1-yl)pyridin-3-yl)methanamine (220 mg). The structure was confirmed by LC-MS.

Synthesis of 1-(5-(aminomethyl)pyridin-2-yl)-1H-pyrazole-4-carbonitrile

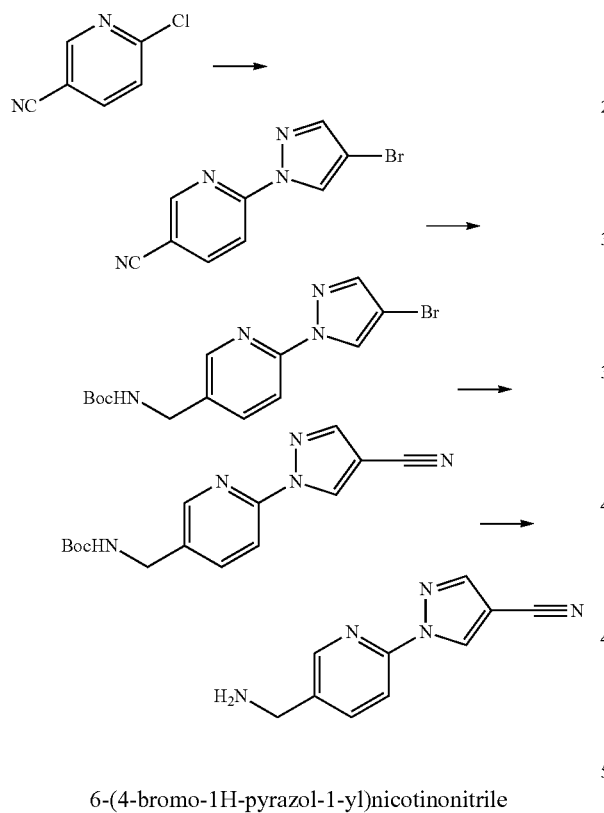

6-(4-bromo-1H-pyrazol-1-yl)nicotinonitrile

To a solution of 6-chloronicotinonitrile (5.0 g, 36.0 mmol) in DMF (5 mL), was added 4-bromo-1H-pyrazole (5.3 g, 36.0 mmol), and Cs$_2$CO$_3$ (23.5 g, 72 mmol). The reaction mixture was stirred at 80° C. for 12 hours. To the reaction mixture was added water and extracted with ethyl acetate. The organic layer was dried with anhydrous Na$_2$SO$_4$, and concentrated under vacuum to give 6.2 g of 6-(4-bromo-1H-pyrazol-1-yl)nicotinonitrile as a light yellow solid. The structure was confirmed by LC-MS.

tert-butyl ((6-(4-bromo-1H-pyrazol-1-yl)pyridin-3-yl)methyl)carbamate

To a solution of 6-(4-bromo-1H-pyrazol-1-yl)nicotinonitrile (1.0 g, 4.0 mmol) in MeOH (10 mL), was added (Boc)$_2$O (1.7 g, 8.0 mmol) and NiCl$_2$ (52 mg, 0.4 mmol), and then added NaBH$_4$ (0.4 g, 10 mmol) slowly at 0° C. The mixture was stirred at 25° C. for 1 hour. To the mixture was added 2 mL of water. The reaction mixture was dried under vacuum, water was added (20 mL), and then extracted with ethyl acetate (20 mL) twice. The organic layer was concentrated under vacuum to give 1.2 g of tert-butyl ((6-(4-bromo-1H-pyrazol-1-yl)pyridin-3-yl)methyl)carbamate. The structure was confirmed by LC-MS.

tert-butyl ((6-(4-cyano-1H-pyrazol-1-yl)pyridin-3-yl)methyl)carbamate

A mixture of tert-butyl ((6-(4-bromo-1H-pyrazol-1-yl)pyridin-3-yl)methyl)carbamate (1.0 g, 2.83 mmol), Zn(CN)2 (200 mg, 1.70 mmol), Zn (185 mg, 2.83 mmol) and Pd(dppf)Cl2 (200 mg, 0.28 mmol) in DMF (10 mL) was stirred at 150° C. for 6 hours. LCMS showed the reaction was completed. The reaction mixture was filtered and the filtrate was evaporated and purified on silica gel (petroleum ether/EtOAc, 10:1 to 5:1 to 2:1) to afford tert-butyl ((6-(4-cyano-1H-pyrazol-1-yl)pyridin-3-yl)methyl)carbamate (440 mg, 52% yield), m/z=299.93 (M+H)+, as a white solid. The structure was confirmed by LC-MS.

1-(5-(aminomethyl)pyridin-2-yl)-1H-pyrazole-4-carbonitrile

A mixture of tert-butyl ((6-(4-cyano-1H-pyrazol-1-yl)pyridin-3-yl)methyl)carbamate (160 mg, 0.53 mmol) in HCl/MeOH(4 M, 4 mL) was stirred at room temperature for 2 hours. LCMS showed the reaction was complete. The reaction mixture was concentrated in vacuo to afford 1-(5-(aminomethyl)pyridin-2-yl)-1H-pyrazole-4-carbonitrile (120 mg, 96% yield), m/z=200.78 (M+H)+, as an off-white solid. The structure was confirmed by LC-MS.

Synthesis of (6-(3-(difluoromethyl)-1H-pyrazol-1-yl)pyridin-3-yl)methanamine

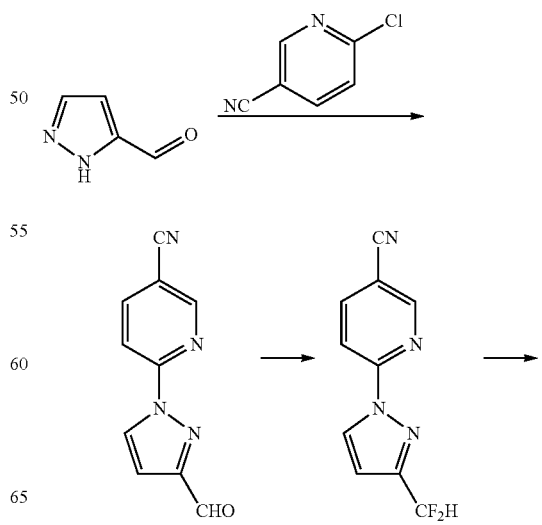

6-(3-formyl-1H-pyrazol-1-yl)nicotinonitrile

To a solution of 1H-pyrazole-5-carbaldehyde (72 mg, 0.75 mmol) and 6-chloronicotinonitrile (75 mg, 0.5 mmol) in 2 mL i-PrOH was added Cs2CO3(100 mg, 0.3 mmol). The resulting mixture was stirred at 100° C. for 2 h. The resulting mixture was concentrated and crude was purified by column flash to give the 6-(3-formyl-1H-pyrazol-1-yl)nicotinonitrile (1.26 g). The structure was confirmed by LC-MS.

6-(3-(difluoromethyl)-1H-pyrazol-1-yl)nicotinonitrile

To a solution of 6-(3-formyl-1H-pyrazol-1-yl)nicotinonitrile (1.26 g, 6.36 mmol) in 120 mL DCM was added DAST (20.0 eq) at −78° C. The reaction mixture was warmed to room temperature overnight, then sat NaHCO$_3$ was added to the mixture until the mixture reached a pH of 7. The reaction mixture was washed with water 3 times. The resulting organic phase was separated and dried over Na$_2$SO$_4$. The crude product was purified by flash column chromatography to obtain 6-(3-(difluoromethyl)-1H-pyrazol-1-yl)nicotinonitrile (745 mg). The structure was confirmed by LC-MS.

tert-butyl ((6-(3-(difluoromethyl)-1H-pyrazol-1-yl)pyridin-3-yl)methyl)carbamate To a solution of 6-(3-(difluoromethyl)-1H-pyrazol-1-yl)nicotinonitrile (745 mg, 3.39 mmol) and (Boc)20 (1.1 g, 5.0) in 20 mL MeOH was added NaBH$_4$ (7.0 eq) at 0° C. The mixture was stirred at room temperature for 30 minutes. The resulting mixture was filtered and concentrated, and the crude product was purified by flash column chromatography to obtain 745 mg of tert-butyl ((6-(3-(difluoromethyl)-1H-pyrazol-1-yl)pyridin-3-yl)methyl)carbamate. The structure was confirmed by LC-MS.

(6-(3-(difluoromethyl)-1H-pyrazol-1-yl)pyridin-3-yl)methanamine

A mixture of tert-butyl ((6-(3-(difluoromethyl)-1H-pyrazol-1-yl)pyridin-3-yl)methyl)carbamate (324 mg, 1 mmol) in 5 mL of HCl/MeOH (6 M) was stirred for 30 minutes at room temperature. The resulting mixture was concentrated to give (6-(3-(difluoromethyl)-1H-pyrazol-1-yl)pyridin-3-yl)methanamine, which was used without further purification. The structure was confirmed by LC-MS.

Synthesis of (5-(4-fluoro-1H-pyrazol-1-yl)pyrazin-2-yl)methanamine

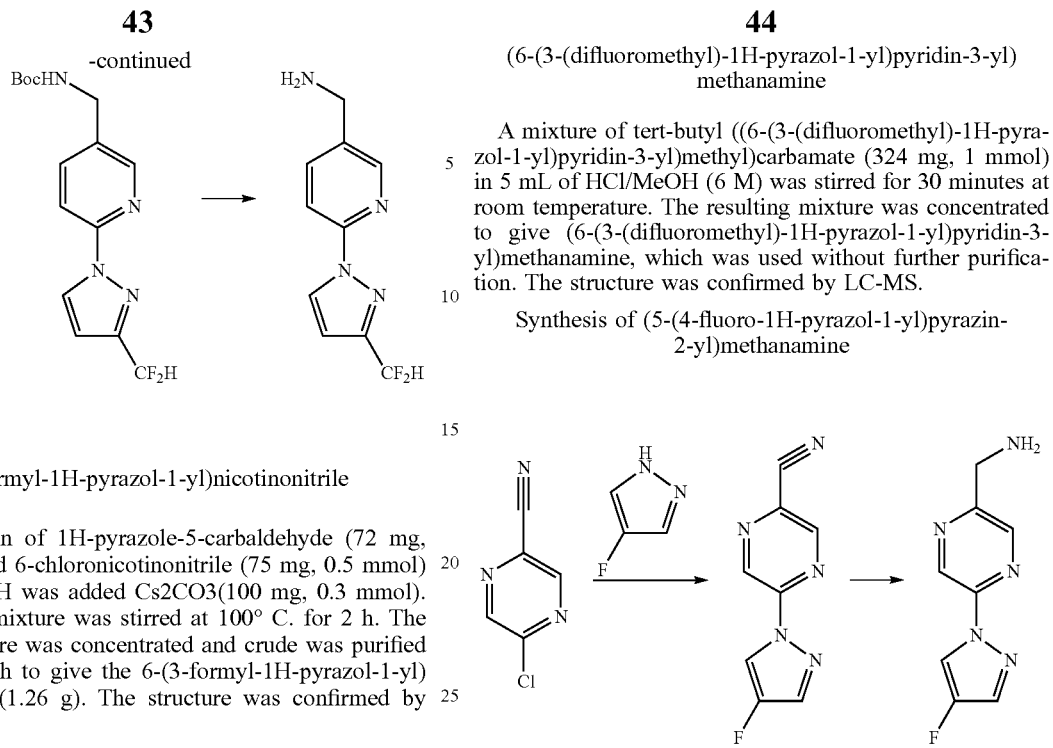

5-(4-fluoro-1H-pyrazol-1-yl)pyrazine-2-carbonitrile

To a solution of 5-chloropyrazine-2-carbonitrile (280 mg, 2.0 mmoL) in DMF was added 4-fluoro-1H-pyrazole (170 mg, 2.0 mmoL), and potassium acetate (395 mg, 4.0 mmoL). The mixture was stirred at the 100° C. for 4 hours. The reaction mixture was cooled to 20° C., poured into brine (25 mL), and extracted with ethyl acetate. The organic layer was dried over sodium sulfate, concentrated and purified by column chromatography (hexane:ethyl acetate=5:1) to give 5-(4-fluoro-1H-pyrazol-1-yl)pyrazine-2-carbonitrile (310 mg, Yield 82%). The structure was confirmed by LC-MS.

(5-(4-fluoro-1H-pyrazol-1-yl)pyrazin-2-yl)methanamine

A mixture of 5-(4-fluoro-1H-pyrazol-1-yl)pyrazine-2-carbonitrile (190 mg, 1.0 mmoL) and NiCl$_2$ (12 mg, 0.1 mmoL) in MeOH (5 mL) was added NaBH$_4$ (380 mg, 10 mmoL) at 0° C. The mixture was stirred at 0° C. for 2 hours, quenched with aqueous NH$_4$Cl and purified by HPLC to give (5-(4-fluoro-1H-pyrazol-1-yl)pyrazin-2-yl)methanamine (160 mg, Yield 82%). The structure was confirmed by LC-MS.

The synthetic protocols that can be used to prepare the compounds disclosed herein are indicated below. The NMR and LC MS data obtained for compounds disclosed herein are also shown below.

| Compound Number | Synthetic Protocol | 1H NMR | MS (M + 1) |
| --- | --- | --- | --- |
| 1 | 1 | $^1$H NMR (300 MHz, DMSO) δ 10.52 (s, 1H), 9.48 (s, 1H), 9.31 (t, J = 6.0 Hz, 1H), 8.81 (d, J = 8.2 Hz, 1H), 8.29 (d, J = 8.2 Hz, 1H), 7.65 (s, 2H), 6.57 (s, 1H), 4.42 (d, J = 6.0 Hz, 2H), 2.51 (s, 3H), 2.32 (s, 3H). | 390 |
| 2 | 1 | $^1$H NMR (301 MHz, DMSO) δ 10.51 (s, 1H), 9.56-9.49 (m, 2H), 8.82 (d, J = 8.2 Hz, 1H), 8.30 (d, J = 8.2 Hz, 1H), 7.41 (t, J = 7.0 Hz, 4H), 7.31 (d, J = 7.0 Hz, 1H), 4.59 (d, J = 6.3 Hz, 2H), 2.56 (s, 3H), 2.32 (s, 3H). | 400 |

-continued

| Compound Number | Synthetic Protocol | 1H NMR | MS (M + 1) |
|---|---|---|---|
| 3 | 1 | ¹H NMR (301 MHz, DMSO) δ 10.68 (s, 1H), 9.70 (s, 1H), 9.47 (s, 1H), 9.04 (s, 1H), 8.81 (d, J = 8.2 Hz, 1H), 8.31 (d, J = 8.2 Hz, 1H), 7.90 (s, 1H), 4.79 (d, J = 6.1 Hz, 2H), 2.53 (s, 3H), 2.33 (s, 3H). | 407 |
| 4 | 1 | 10.52 (br s, 1H) 9.52 (s, 1H) 8.78 (d, 1H) 8.09 (d, 1H) 7.48 (m, 1H) 7.37 (m, 3H) 7.25 (br s, 1H) 5.18 (s, 2H) 5.00 (s, 2H) 2.56 (s, 3H) 2.33 (s, 3H) | 412 |
| 5 | 1 | ¹H NMR (301 MHz, DMSO) δ 12.10 (s, 1H), 9.95 (s, 1H), 9.54 (s, 1H), 9.43 (s, 1H), 8.84 (dd, J = 8.1, 1.4 Hz, 1H), 8.24 (d, J = 8.2 Hz, 1H), 7.30 (d, J = 7.8 Hz, 2H), 7.18 (d, J = 7.8 Hz, 2H), 4.53 (d, J = 6.1 Hz, 2H), 2.45 (s, 3H), 2.31 (s, 3H). | 414 |
| 6 | 1 | ¹H NMR (301 MHz, DMSO) δ 10.38 (s, 1H), 9.52 (s, 1H), 9.24 (d, J = 8.5 Hz, 1H), 8.82 (dd, J = 8.1, 1.5 Hz, 1H), 8.25 (d, J = 8.2 Hz, 1H), 7.51 (d, J = 7.5 Hz, 2H), 7.39 (t, J = 7.4 Hz, 2H), 7.30 (s, 1H), 5.32-5.23 (m, 1H), 2.50 (s, 3H), 2.33 (s, 3H), 1.62 (d, J = 7.0 Hz, 3H). | 414 |
| 7 | 1 | 12.03 (s, 1H) 9.9 (s, 1H) 9.5 (s, 1H) 9.43 (m, 1H) 8.78 (d, 1H) 8.36 (s, 1H) 8.19(d, 1H) 7.56 (d, 1H) 7.24 (d, 1H) 4.59 (d, 2H) 2.39 (s, 3H) 2.25 (s, 3H) 2.24 (s, 3H) | 415 |
| 8 | 1 | ¹H NMR (301 MHz, DMSO) δ 10.36 (s, 1H), 9.62 (s, 1H), 9.52 (s, 1H), 8.83 (dd, J = 8.2, 1.8 Hz, 1H), 8.28 (d, J = 8.2 Hz, 1H), 7.43 (d, J = 6.3 Hz, 1H), 7.24 (t, J = 9.4 Hz, 2H), 7.15 (d, J = 9.0 Hz, 1H), 4.60 (d, J = 6.3 Hz, 2H), 2.50 (s, 3H), 2.32 (s, 3H). | 418 |
| 9 | 1 | ¹H NMR (301 MHz, DMSO) δ 10.37 (s, 1H), 9.54 (d, J = 17.7 Hz, 2H), 8.82 (d, J = 8.2 Hz, 1H), 8.28 (d, J = 8.2 Hz, 1H), 7.50-7.41 (m, 2H), 7.20 (t, J = 8.8 Hz, 2H), 4.56 (d, J = 6.2 Hz, 2H), 2.50 (s, 3H), 2.32 (s, 3H). | 418 |
| 10 | 1 | ¹H NMR (301 MHz, DMSO) δ 10.35 (s, 1H), 9.50 (s, 1H), 9.43 (s, 1H), 8.82 (dd, J = 8.2, 1.7 Hz, 1H), 8.27 (d, J = 8.2 Hz, 1H), 7.35 (d, J = 8.5 Hz, 2H), 6.94 (d, J = 8.5 Hz, 2H), 4.51 (d, J = 6.2 Hz, 2H), 3.78 (s, 3H), 2.49 (s, 3H), 2.32 (s, 3H). | 430 |
| 11 | 1 | ¹H NMR (301 MHz, DMSO) δ 10.34 (s, 1H), 9.60 (s, 1H), 9.52 (s, 1H), 8.83 (d, J = 8.1 Hz, 1H), 8.27 (d, J = 8.2 Hz, 1H), 7.44 (s, 4H), 4.57 (d, J = 6.3 Hz, 2H), 2.49 (s, 3H), 2.32 (s, 3H). | 434 |
| 12 | 1 | ¹H NMR (400 MHz, DMSO) δ 10.49 (s, 1H), 9.42 (d, J = 7.0 Hz, 2H), 8.76 (dd, J = 8.2, 2.0 Hz, 1H), 8.24 (d, J = 8.2 Hz, 1H), 7.28 (d, J = 8.7 Hz, 2H), 6.89-6.85 (m, 2H), 4.45 (d, J = 6.3 Hz, 2H), 3.99 (d, J = 7.0 Hz, 2H), 2.45 (s, 3H), 2.27 (s, 3H), 1.31 (s, 3H). | 444 |
| 13 | 2 | ¹H NMR (400 MHz, DMSO) δ 10.54 (s, 1H), 9.26-9.14 (m, 2H), 8.49 (d, J = 1.3 Hz, 1H), 7.28 (d, J = 8.6 Hz, 2H), 6.89 (d, J = 8.6 Hz, 2H), 6.27 (s, 1H), 4.41 (d, J = 6.2 Hz, 2H), 4.00 (q, J = 7.0 Hz, 2H), 2.63 (s, 3H), 2.46 (s, 3H), 2.26 (s, 3H), 1.31 (t, J = 7.0 Hz, 3H). | 458 |
| 14 | 1 | ¹H NMR (400 MHz, DMSO) δ 10.52 (s, 1H), 9.44-9.37 (m, 2H), 8.76 (dd, J = 8.2, 2.1 Hz, 1H), 8.24 (d, J = 8.2 Hz, 1H), 7.27 (d, J = 8.7 Hz, 2H), 6.86 (d, J = 8.7 Hz, 2H), 4.60-4.54 (m, 1H), 4.45 (d, J = 6.3 Hz, 2H), 2.46 (s, 3H), 2.27 (s, 3H), 1.24 (d, J = 6.0 Hz, 6H). | 458 |
| 15 | 1 | ¹H NMR (400 MHz, DMSO) δ 10.39 (s, 1H), 9.55 (t, J = 6.4 Hz, 1H), 9.45 (d, J = 1.6 Hz, 1H), 8.77 (dd, J = 8.2, 2.1 Hz, 1H), 8.23 (d, J = 8.3 Hz, 1H), 7.41 (d, J = 8.7 Hz, 2H), 7.14 (d, J = 8.6 Hz, 2H), 4.51 (d, J = 6.3 Hz, 2H), 2.45 (s, 3H), 2.27 (s, 3H). | 466 |
| 16 | 2 | ¹H NMR (400 MHz, DMSO) δ 10.77 (s, 1H), 9.21 (s, 1H), 8.98 (d, J = 8.5 Hz, 1H), 8.47 (d, J = 1.8 Hz, 1H), 7.34 (d, J = 8.7 Hz, 2H), 6.89 (d, J = 8.7 Hz, 2H), 5.15-5.10 (m, 1H), 4.00 (q, J = 7.0 Hz, 2H), 2.56 (s, 3H), 2.48 (s, 3H), 2.27 (s, 3H), 1.48 (d, J = 7.0 Hz, 3H), 1.32 (t, J = 7.0 Hz, 3H). | 472 |
| 17 | 2 | ¹H NMR (400 MHz, DMSO) δ 10.65 (s, 1H), 9.21 (s, 1H), 8.97 (d, J = 8.5 Hz, 1H), 8.47 (d, J = 1.4 Hz, 1H), 7.34 (d, J = 8.6 Hz, 2H), 6.89 (d, J = 8.7 Hz, 2H), 5.12 (d, J = 7.7 Hz, 1H), 4.00 (q, J = 7.0 Hz, 2H), 2.56 (s, 3H), 2.47 (s, 3H), 2.27 (s, 3H), 1.48 (d, J = 7.0 Hz, 3H), 1.31 (t, J = 7.0 Hz, 3H). | 472 |
| 18 | 1 | 1H NMR (301 MHz, DMSO) δ 10.48 (s, 1H), 9.63 (s, 1H), 9.45 (s, 1H), 8.76 (d, J = 6.6 Hz, 1H), 8.43 (s, 1H), 8.36 (s, 1H), 8.24 (d, J = 8.2 Hz, 1H), 7.94 (d, J = 7.4 Hz, 1H), 7.84 (d, J = 8.4 Hz, 1H), 7.61 (s, 1H), 7.21-6.89 (m, 1H), 6.42-6.11 (m, 1H), 4.57 (d, J = 6.2 Hz, 2H), 2.45 (s, 3H), 2.27 (s, 3H), 2.10 (s, 3H). | 481 |

| Compound Number | Synthetic Protocol | 1H NMR | MS (M + 1) |
|---|---|---|---|
| 19 | 2 | ¹H NMR (400 MHz, DMSO) δ 10.49 (s, 1H), 9.44 (s, 1H), 9.25 (s, 1H), 8.61 (d, J = 2.2 Hz, 1H), 8.51 (d, J = 1.3 Hz, 1H), 8.47 (d, J = 1.6 Hz, 1H), 7.98 (dd, J = 8.5, 2.1 Hz, 1H), 7.92 (d, J = 8.4 Hz, 1H), 7.81 (d, J = 1.0 Hz, 1H), 7.11 (s, 1H), 6.59-6.55 (m, 1H), 6.28 (s, 1H), 4.55 (d, J = 6.1 Hz, 2H), 2.65 (s, 3H), 2.45 (s, 3H), 2.26 (s, 3H). | 481 |
| 20 | 1 | 1H NMR (400 MHz, DMSO) δ 10.42 (s, 1H), 9.61 (t, J = 6.4 Hz, 1H), 9.46 (d, J = 1.9 Hz, 1H), 8.77 (dd, J = 8.2, 2.1 Hz, 1H), 8.23 (d, J = 8.2 Hz, 1H), 7.48 (d, J = 8.7 Hz, 2H), 7.33 (d, J = 8.0 Hz, 2H), 4.55 (d, J = 6.4 Hz, 2H), 2.45 (s, 3H), 2.27 (s, 3H). | 483 |
| 21 | 1 | ¹H NMR (400 MHz, DMSO) δ 10.00 (s, 1H), 9.60 (s, 1H), 9.52 (s, 1H), 9.15 (s, 1H), 8.81 (d, J = 10.0 Hz, 1H), 8.73 (s, 1H), 8.55 (s, 1H), 8.21 (d, J = 8.1 Hz, 1H), 8.04 (d, J = 4.2 Hz, 1H), 4.75 (d, J = 6.1 Hz, 3H), 2.42 (s, 2H), 2.26 (s, 3H). | 486 |
| 22 | 1 | 1H NMR (400 MHz, DMSO) δ 10.39 (s, 1H), 9.70 (t, J = 6.3 Hz, 1H), 9.47 (d, J = 1.5 Hz, 1H), 9.43-9.36 (m, 1H), 8.78 (dd, J = 8.2, 2.1 Hz, 1H), 8.54 (d, J = 1.8 Hz, 1H), 8.43-8.38 (m, 1H), 8.24 (d, J = 8.1 Hz, 1H), 8.05 (dd, J = 8.5, 2.2 Hz, 1H), 7.96 (d, J = 8.4 Hz, 1H), 7.14 (s, 1H), 6.31 (s, 1H), 4.61 (d, J = 6.2 Hz, 2H), 2.45 (s, 3H), 2.27 (s, 3H). | 492 |
| 23 | 2 | ¹H NMR (400 MHz, DMSO) δ 10.36 (s, 1H), 9.30-9.19 (m, 2H), 8.61 (d, J = 2.5 Hz, 1H), 8.54 (d, J = 2.0 Hz, 1H), 8.50 (s, 1H), 8.10-8.03 (m, 1H), 7.92 (d, J = 8.5 Hz, 1H), 7.81 (s, 1H), 6.60-6.54 (m, 1H), 5.25 (d, J = 7.4 Hz, 1H), 2.56 (s, 3H), 2.44 (s, 3H), 2.26 (s, 3H), 1.58 (d, J = 7.0 Hz, 3H). | 495 |
| 24 | 1 | ¹H NMR (400 MHz, DMSO) δ 10.53 (s, 1H), 9.65 (t, J = 6.3 Hz, 1H), 9.45 (d, J = 1.4 Hz, 1H), 8.77 (dd, J = 8.2, 2.1 Hz, 1H), 8.44 (s, 1H), 8.26 (d, J = 8.2 Hz, 1H), 7.92 (d, J = 8.5 Hz, 1H), 7.77 (d, J = 8.4 Hz, 1H), 6.10 (s, 1H), 4.58 (d, J = 6.2 Hz, 2H), 2.56 (s, 3H), 2.46 (s, 3H), 2.27 (s, 3H), 2.19 (s, 3H). | 495 |
| 25 | 1 | (400 MHz, DMSO-d6) δ 12.03 (s, 1H), 9.90 (s, 1H), 9.51 (d, J = 2.0 Hz, 1H), 9.39 (d, J = 8.3 Hz, 1H), 8.77 (dd, J = 8.2, 2.1 Hz, 1H), 8.66 (d, J = 4.5 Hz, 1H), 8.53 (d, J = 2.2 Hz, 1H), 8.15 (d, J = 8.2 Hz, 1H), 8.09 (dd, J = 8.6, 2.3 Hz, 1H), 7.92-7.86 (m, 2H), 5.30 (p, J = 7.1 Hz, 1H), 2.39 (s, 3H), 2.25 (s, 3H), 1.61 (d, J = 7.0 Hz, 3H). | 499 |
| 26 | 1 | 1H NMR (400 MHz, DMSO) δ 10.44 (s, 1H), 9.65 (s, 1H), 9.46 (d, J = 1.6 Hz, 1H), 8.77 (s, 1H), 8.43 (dd, J = 7.7, 2.2 Hz, 2H), 8.24 (d, J = 8.2 Hz, 1H), 7.92 (d, J = 2.2 Hz, 1H), 7.81 (d, J = 8.4 Hz, 1H), 6.26 (d, J = 2.6 Hz, 1H), 4.56 (d, J = 6.2 Hz, 2H), 2.27 (s, 3H), 2.04-1.93 (m, 1H), 0.94 (dd, J = 8.4, 2.4 Hz, 2H), 0.75 (dd, J = 4.9, 2.3 Hz, 2H). | 507 |
| 27 | 1 | ¹H NMR (400 MHz, DMSO) δ 10.40 (s, 1H), 9.65 (t, J = 6.2 Hz, 1H), 9.46 (d, J = 1.6 Hz, 1H), 8.78 (dd, J = 8.2, 2.1 Hz, 1H), 8.43 (d, J = 1.8 Hz, 1H), 8.35 (s, 1H), 8.24 (d, J = 8.2 Hz, 1H), 7.94 (dd, J = 8.5, 2.2 Hz, 1H), 7.84 (d, J = 8.4 Hz, 1H), 7.62 (s, 1H), 4.57 (d, J = 6.3 Hz, 2H), 2.45 (s, 3H), 2.27 (s, 3H), 0.90-0.85 (m, 2H), 0.64-0.59 (m, 2H). | 507 |
| 28 | 1 | ¹H NMR (400 MHz, DMSO) δ 12.06 (s, 1H), 9.93 (s, 1H), 9.62 (t, J = 6.3 Hz, 1H), 9.50 (d, J = 1.4 Hz, 1H), 8.80 (dd, J = 8.2, 2.1 Hz, 1H), 8.46-8.39 (m, 2H), 8.20 (d, J = 8.6 Hz, 1H), 7.94 (dd, J = 8.5, 2.2 Hz, 1H), 7.85 (d, J = 8.5 Hz, 1H), 7.66 (s, 1H), 4.71 (t, J = 5.2 Hz, 1H), 4.57 (d, J = 6.2 Hz, 2H), 3.62-3.57 (m, 2H), 2.64 (t, J = 6.8 Hz, 2H), 2.40 (s, 3H), 2.26 (s, 3H). | 511 |
| 29 | 3 | ¹H NMR (400 MHz, DMSO) δ 10.73 (s, 1H), 9.25 (dd, J = 12.9, 5.0 Hz, 2H), 8.69 (dd, J = 4.6, 0.8 Hz, 1H), 8.54 (d, J = 2.2 Hz, 1H), 8.49 (d, J = 1.4 Hz, 1H), 8.08 (dd, J = 8.6, 2.3 Hz, 1H), 7.92 (dd, J = 4.6, 3.8 Hz, 2H), 7.21-7.05 (m, 1H), 6.38-6.19 (m, 1H), 5.31-5.23 (m, 1H), 2.56 (s, 3H), 2.48 (s, 3H), 2.27 (s, 3H), 1.58 (d, J = 7.1 Hz, 3H). | 513 |
| 30 | 3 | (400 MHz, DMSO-d6) δ 12.06 (s, 1H), 9.97 (s, 1H), 9.35 (d, J = 8.1 Hz, 1H), 9.31 (s, 1H), 8.69 (d, J = 4.5 Hz, 1H), 8.52 (d, J = 2.3 Hz, 1H), 8.42 (d, J = 11.4 Hz, 1H), 8.06 (dd, J = 8.4, 2.3 Hz, 1H), 7.95-7.86 (m, 2H), | 517 |

-continued

| Compound Number | Synthetic Protocol | 1H NMR | MS (M + 1) |
|---|---|---|---|
| | | 5.26 (p, J = 7.1 Hz, 1H), 2.39 (s, 3H), 2.24 (s, 3H), 1.56 (d, J = 7.0 Hz, 3H). | |
| 31 | 1 | $^1$H NMR (400 MHz, DMSO) δ 10.41 (s, 1H), 9.68 (t, J = 6.3 Hz, 1H), 9.46 (d, J = 1.5 Hz, 1H), 8.91 (s, 1H), 8.78 (dd, J = 8.2, 2.1 Hz, 1H), 8.51 (d, J = 1.8 Hz, 1H), 8.24 (d, J = 8.1 Hz, 1H), 8.08 (s, 1H), 8.02 ( dd, J = 8.5, 2.2 Hz, 1H), 7.94 (d, J = 8.4 Hz, 1H), 7.14 (t, J = 55.8 Hz, 1H), 4.60 (d, J = 6.3 Hz, 2H), 2.51 (dt, J = 3.5, 1.7 Hz, 14H), 2.45 (s, 3H), 2.27 (s, 3H). | 517 |
| 32 | 1 | $^1$H NMR (400 MHz, DMSO) δ 10.22 (s, 1H), 9.66 (t, J = 6.2 Hz, 1H), 9.48 (d, J = 1.7 Hz, 1H), 8.79 (dd, J = 9.9, 1.7 Hz, 2H), 8.48 (d, J = 2.0 Hz, 1H), 8.23 (d, J = 8.2 Hz, 1H), 7.98 (dd, J = 8.5, 2.2 Hz, 1H), 7.87 (d, J = 8.4 Hz, 1H), 7.26 (s, 0.2H), 7.12 (s, 0.5H), 6.98 (s, 0.3H), 4.58 (d, J = 6.3 Hz, 2H), 2.43 (s, 3H), 2.36 (s, 3H), 2.26 (s, 3H). | 531 |
| 33 | 1 | $^1$H NMR (400 MHz, DMSO-d$_6$) δ 12.03 (s, 1H), 9.91 (s, 1H), 9.51 (d, J = 2.0 Hz, 1H), 9.30 (d, J = 8.0 Hz, 1H), 9.17 (d, J = 1.4 Hz, 1H), 8.79 (dd, J = 8.2, 2.2 Hz, 1H), 8.72 (d, J = 4.5 Hz, 1H), 8.65 (d, J = 1.5 Hz, 1H), 8.17 (d, J = 8.2 Hz, 1H), 8.03 (d, J = 4.2 Hz, 1H), 5.41 (p, J = 7.1 Hz, 1H), 2.39 (s, 3H), 2.25 (s, 3H), 1.62 (d, J = 7.0 Hz, 3H) | 500 |
| 34 | 1 | $^1$H NMR (400 MHz, DMSO-d$_6$) δ 12.03 (s, 1H), 9.90 (s, 1H), 9.51 (d, J = 2.1 Hz, 1H), 9.39 (d, J = 8.7 Hz, 1H), 8.77 (dd, J = 8.2, 2.1 Hz, 1H), 8.66 (d, J = 4.5 Hz, 1H), 8.53 (d, J = 2.2 Hz, 1H), 8.17-8.08 (m, 2H), 7.93-7.85 (m, 2H), 5.04 (q, J = 8.3 Hz, 1H), 2.38 (s, 3H), 2.25 (s, 3H), 2.07 (dt, J = 15.6, 7.7 Hz, 1H), 1.93 (dt, J = 13.7, 6.9 Hz, 1H), 0.91 (t, J = 7.2 Hz, 3H) | 513 |
| 35 | 1 | $^1$H NMR (400 MHz, DMSO-d$_6$) δ 12.03 (s, 1H), 9.90 (s, 1H), 9.54-9.47 (m, 1H), 9.40 (d, J = 8.4 Hz, 1H), 8.77 (dd, J = 8.2, 2.1 Hz, 1H), 8.66 (d, J = 4.5 Hz, 1H), 8.53 (d, J = 2.3 Hz, 1H), 8.14 (d, J = 8.2 Hz, 1H), 8.09 (dd, J = 8.6, 2.3 Hz, 1H), 7.93-7.83 (m, 2H), 5.30 (p, J = 7.1 Hz, 1H), 2.39 (s, 3H), 2.25 (s, 3H), 1.61 (d, J = 7.1 Hz, 3H). | 499 |

Example 4: Measurement of Biochemical Activity of Compounds

In order to assess the activity of chemical compounds against the relevant kinase of interest, the Caliper Life-Sciences electrophoretic mobility shift technology platform is used. Fluorescently labeled substrate peptide is incubated in the presence of kinase and ATP so that a reflective proportion of the peptide is phosphorylated. At the end of the reaction, the mix of phosphorylated (product) and non-phosphorylated (substrate) peptides are passed through the microfluidic system of the Caliper EZ Reader 2, under an applied potential difference. The presence of the phosphate group on the product peptide provides a difference in mass and charge between those of the substrate peptide, resulting in a separation of the substrate and product pools in the sample. As the pools pass a LEDS within the instrument, these pools are detected and resolved as separate peaks. The ratio between these peaks therefore reflects the activity of the chemical matter at that concentration in that well, under those conditions.

RET Wild Type Assay at KM

In each well of a 384-well plate, 7.5 nM-10 nM of wild type RET (ProQinase 1090-0000-1) is incubated in a total of 12.5 μL of buffer (100 mM HEPES pH 7.5, 0.015% Brij 35, 10 mM MgCl$_2$, 1 mM DTT) with 1 μM CSKtide (FITC-AHA-KKKKD DIYFFFG-NH2) and 25 μM ATP at 25° C. for 120 minutes in the presence or absence of a dosed concentration series of compound (1% DMSO final concentration). The reaction is stopped by the addition of 70 μL of Stop buffer (100 mM HEPES pH 7.5, 0.015% Brij 35, 35 mM EDTA and 0.2% of Coating Reagent 3 (Caliper Lifesciences)). The plate is then read on a Caliper EZReader 2 (protocol settings: −1.7 psi, upstream voltage −500, downstream voltage −3000, post sample sip 35s). Data is normalized to 0% and 100% inhibition controls and the IC$_{50}$ calculated using a 4-parameter fit in the CORE LIMS.

RET V804L Gatekeeper Mutant Assay at KM

In each well of a 384-well plate, 7.5 nM-10 nM of mutant RET (ProQinase 1096-0000-1) is incubated in a total of 12.5 μL of buffer (100 mM HEPES pH 7.5, 0.015% Brij 35, 10 mM MgCl2, 1 mM DTT) with 1 μM CSKtide (FITC-AHA-KKKKDDIYFFFG-NH2) and 10 μM ATP at 25° C. for 120 minutes in the presence or absence of a dosed concentration series of compound (1% DMSO final concentration). The reaction is stopped by the addition of 70 μL of Stop buffer (100 mM HEPES pH 7.5, 0.015% Brij 35, 35 mM EDTA and 0.2% of Coating Reagent 3 (Caliper Lifesciences)). The plate is then read on a Caliper EZReader 2 (protocol settings: −1.7 psi, upstream voltage −500, downstream voltage −3000, post sample sip 35s). Data is normalized to 0% and 100% inhibition controls and the IC$_{50}$ calculated using a 4-parameter fit in the CORE LIMS.

In the Table below, the following designations are used: <10.00 nM=A; 10.01-100.0 nM=B; >100 nM=C; and ND=not determined.

| Compound Number | Wild-type RET | V804L Mutant |
|---|---|---|
| 1 | B | B |
| 2 | B | B |
| 3 | C | C |
| 4 | B | B |
| 5 | B | B |
| 6 | C | B |
| 7 | B | B |
| 8 | C | B |
| 9 | B | B |
| 10 | B | B |
| 11 | B | A |
| 12 | B | B |
| 13 | B | ND |
| 14 | B | B |
| 15 | B | B |
| 16 | C | ND |
| 17 | C | ND |
| 18 | A | A |
| 19 | A | A |
| 20 | C | C |
| 21 | A | A |
| 22 | B | B |
| 23 | A | A |
| 24 | A | A |
| 25 | A | A |
| 26 | A | A |
| 27 | B | C |
| 28 | B | A |
| 29 | A | A |
| 30 | A | A |
| 31 | B | B |
| 32 | B | B |
| 33 | A | C |
| 34 | A | C |
| 35 | A | C |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of Formula (I) or a pharmaceutically acceptable salt thereof, wherein:

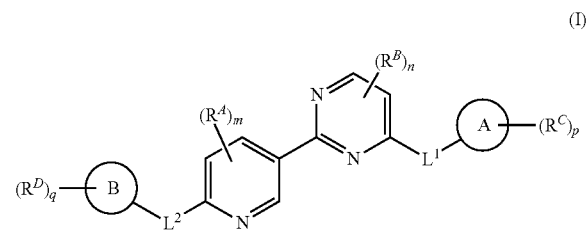

(I)

ring A is 1H-pyrazol-3-yl;
ring B is selected from aryl, heteroaryl, cycloalkyl, and heterocyclyl;
$L^1$ is —NH—;
$L^2$ is selected from —($C_1$-$C_6$ alkylene)-, —($C_2$-$C_6$ alkenylene)-, —($C_2$-$C_6$ alkynylene)-, —($C_1$-$C_6$ haloalkylene)-, —($C_1$-$C_6$ heteroalkylene)-, —C(O)—, —O—, —S—, —S(O), —S(O)$_2$—, —N($R^1$)—, —O—($C_1$-$C_6$ alkylene)-, —($C_1$-$C_6$ alkylene)-O—, —N($R^1$)—C(O)—, —C(O)—N($R^1$)—, —($C_1$-$C_6$ alkylene)-N($R^1$)—, —N($R^1$)—($C_1$-$C_6$ alkylene)-, —N($R^1$)—C(O)—($C_1$-$C_6$ alkylene)-, —($C_1$-$C_6$ alkylene)-N($R^1$)—C(O)—, —C(O)—N($R^1$)—($C_1$-$C_6$ alkylene)-, —($C_1$-$C_6$ alkylene)-C(O)—N($R^1$)—, —N($R^1$)—S(O)$_2$—, —S(O)$_2$—N($R^1$)—, —N($R^1$)—S(O)$_2$—($C_1$-$C_6$ alkylene)-, and S(O)$_2$—N($R^1$)—($C_1$-$C_6$ alkylene)-, wherein each alkylene, alkenylene, alkynylene, haloalkylene, and heteroalkylene is independently substituted with 0-5 occurrences of R';

each $R^A$ is independently selected from $C_1$-$C_6$ alkyl, $C_1$-$C_6$ alkoxy, halo, $C_1$-$C_6$ haloalkyl, $C_1$-$C_6$ hydroxyalkyl, $C_1$-$C_6$ heteroalkyl, and —N($R^1$)($R^1$), wherein each alkyl, alkoxy, haloalkyl, hydroxyalkyl, and hydroxyalkyl is independently substituted with 0-5 occurrences of $R^a$;

$R^B$ is selected from $C_1$-$C_6$ alkyl, $C_1$-$C_6$ alkoxy, $C_1$-$C_6$ haloalkyl, and $C_1$-$C_6$ hydroxyalkyl;

$R^C$ is selected from $C_1$-$C_6$ alkyl, $C_2$-$C_6$ alkenyl, $C_2$-$C_6$ alkynyl, $C_1$-$C_6$ alkoxy, $C_1$-$C_6$ heteroalkyl, $C_1$-$C_6$ haloalkyl, and $C_1$-$C_6$ hydroxyalkyl;

each $R^D$ is independently selected from $C_1$-$C_6$ alkyl, $C_2$-$C_6$ alkenyl, $C_2$-$C_6$ alkynyl, $C_1$-$C_6$ alkoxy, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —($C_1$-$C_6$ alkylene)-C(O)$R^1$, —S$R^1$, —S(O)$_2R^1$, —S(O)$_2$—N($R^1$)($R^1$), —($C_1$-$C_6$ alkylene)-S(O)$_2R^1$, —($C_1$-$C_6$ alkylene)-S(O)$_2$—N($R^1$)($R^1$), —N($R^1$)($R^1$), —C(O)—N($R^1$)($R^1$), —N($R^1$)—C(O)$R^1$, —N($R^1$)—C(O)O$R^1$, —($C_1$-$C_6$ alkylene)-N($R^1$)—C(O)$R^1$, —N($R^1$)S(O)$_2R^1$, and —P(O)($R^1$)($R^1$), wherein each of alkyl, alkenyl, alkynyl, alkoxy, heteroalkyl, haloalkyl, haloalkoxy, hydroxyalkyl, cycloalkyl, aryl, heteroaryl, aryloxy, aralkyl, heterocyclyl, and heterocyclylalkyl is independently substituted with 0-5 occurrences of $R^a$, or 2 $R^C$ or 2 $R^D$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, $C_1$-$C_6$ alkyl, $C_1$-$C_6$ thioalkyl, $C_1$-$C_6$ alkoxy, $C_1$-$C_6$ haloalkyl, $C_1$-$C_6$ hydroxyalkyl, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxy, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

each $R^a$ and $R^b$ is independently $C_1$-$C_6$ alkyl, halo, hydroxyl, $C_1$-$C_6$ haloalkyl, $C_1$-$C_6$ heteroalkyl, $C_1$-$C_6$ hydroxyalkyl, $C_1$-$C_6$ alkoxy, cycloalkyl, heterocyclyl, or cyano, wherein each of alkyl, haloalkyl, heteroalkyl, hydroxyalkyl, alkoxy, cycloalkyl, and heterocyclyl is independently substituted with 0-5 occurrences of R';

each R' is $C_1$-$C_6$ alkyl, $C_1$-$C_6$ heteroalkyl, halo, hydroxyl, $C_1$-$C_6$ haloalkyl, $C_1$-$C_6$ hydroxyalkyl, cycloalkyl, or cyano, or 2 R' together with the atom(s) to which they are attached form a cycloalkyl or heterocyclyl ring;
m is 0, 1, 2, or 3;
n is 1;
p is 1; and
q is 0, 1, 2, 3, or 4.

2. The compound of claim 1 or a pharmaceutically acceptable salt thereof, wherein the portion of the compound represented by

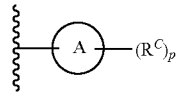

is 5-methyl-1H-pyrazol-1-yl.

3. The compound of claim 1 or a pharmaceutically acceptable salt thereof, $L^2$ is selected from *—C(O)—, *—N($R^1$)—C(O)—, and *—($C_1$-$C_6$ alkylene)-N($R^1$)—C(O)—, wherein the $C_1$-$C_6$ alkylene portion of $L^2$ is substituted with 0-5 occurrences of R', and wherein "*" represents a portion of $L^2$ bound to ring B.

4. The compound of claim 3 or a pharmaceutically acceptable salt thereof, wherein $L^2$ is selected from *—C(O)— and *—($C_1$-$C_6$ alkylene)-N($R^1$)—C(O)—, wherein the $C_1$-$C_6$ alkylene portion of $L^2$ is substituted with 0-5 occurrences of R'.

5. The compound of claim 1 having structural Formula I(b):

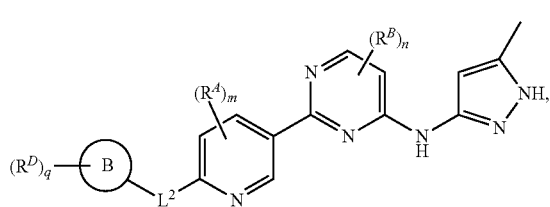

I(b)

or a pharmaceutically acceptable salt thereof, wherein $L^2$ is —C(O)—N($R^1$)—($C_1$-$C_6$ alkylene)-, and wherein $C_1$-$C_6$ alkylene is substituted with 0-5 occurrences of R'.

6. The compound of claim 3 or a pharmaceutically acceptable salt thereof, wherein $L^2$ is selected from *—C(O)—, *—$CH_2$—NH—C(O)—, *—CH($CH_3$)—NH—C(O)—, and *—CH($CH_2CH_3$)—NH—C(O)—.

7. The compound of claim 5 having structural Formula I(c):

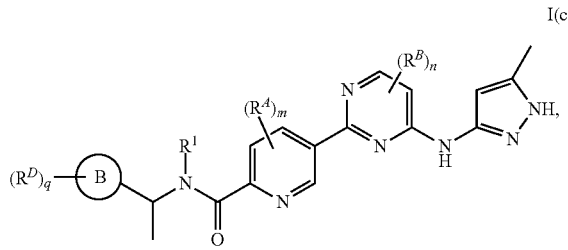

I(c)

or a pharmaceutically acceptable salt thereof.

8. The compound of claim 7 having structural Formula I(d):

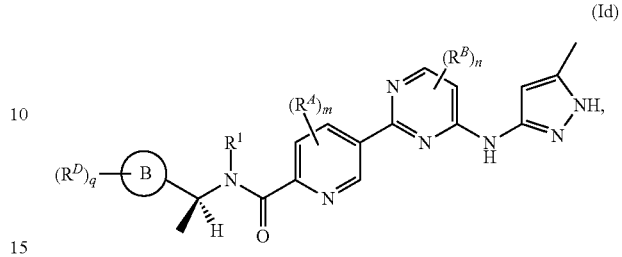

(Id)

or a pharmaceutically acceptable salt thereof.

9. The compound of claim 7 having structural Formula I(e):

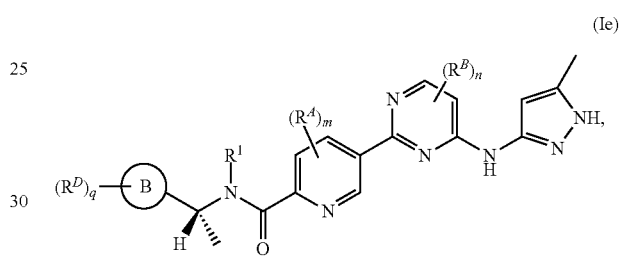

(Ie)

or a pharmaceutically acceptable salt thereof.

10. The compound of claim 1 or a pharmaceutically acceptable salt thereof, wherein $R^1$ is hydrogen.

11. The compound of claim 1 or a pharmaceutically acceptable salt thereof, wherein:
m is 0 or 1; or
q is 0, 1, or 2.

12. The compound of claim 11 or a pharmaceutically acceptable salt thereof, wherein:
m is 0, or
m is 1 and $R^A$ is methyl or fluoro;
$R^B$ is methyl; or
q is 1 or 2 and each $R^D$ is independently selected from fluoro, chloro, methyl, —O—$CH_3$, —O—$CH_2CH_3$, —O—CH($CH_3$)$_2$, —O—$CHF_2$, —O—$CF_3$, and 1H-pyrazol-1-yl independently substituted with 0-5 occurrences of $R^a$.

13. The compound of claim 12 or a pharmaceutically acceptable salt thereof, wherein each $R^D$ is independently selected from fluoro, chloro, methyl, —O—$CH_3$, —O—$CH_2CH_3$, —O—CH($CH_3$)$_2$, —O—$CHF_2$, —O—$CF_3$, 4-methyl-1H-pyrazol-1-yl, 1H-pyrazol-1-yl, 4-fluoro-1H-pyrazol-1-yl, 4-cyano-1H-pyrazol-1-yl, 3,5-dimethyl-1H-pyrazol-1-yl, 3-cyclopropyl-1H-pyrazol-1-yl, 4-cyclopropyl-1H-pyrazol-1-yl, 4-(1-hydroxyethyl)-1H-pyrazol-1-yl, 4-difluoromethyl-1H-pyrazol-1-yl, and 3-methyl-4-difluoromethyl-1H-pyrazol-1-yl.

14. The compound of claim 1 or a pharmaceutically acceptable salt thereof, wherein the compound or the pharmaceutically acceptable salt thereof is selected from any one of the following compounds and pharmaceutically acceptable salts thereof:

| Compound | Structure |
|---|---|
| 1 | 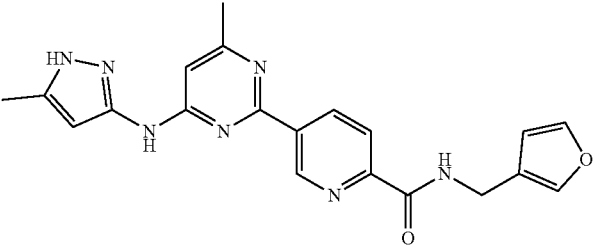 [SMILES: Cc1cc(Nc2cc(C)[nH]n2)nc(-c2ccc(C(=O)NCc3ccoc3)nc2)n1] |
| 2 | 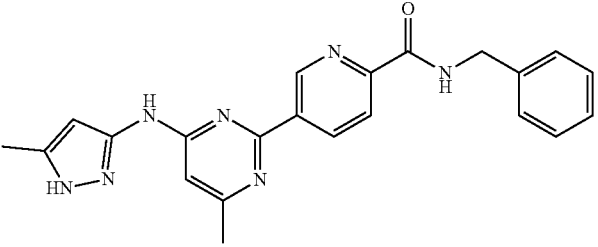 [SMILES: Cc1cc(Nc2cc(C)[nH]n2)nc(-c2ccc(C(=O)NCc3ccccc3)nc2)n1] |
| 3 | 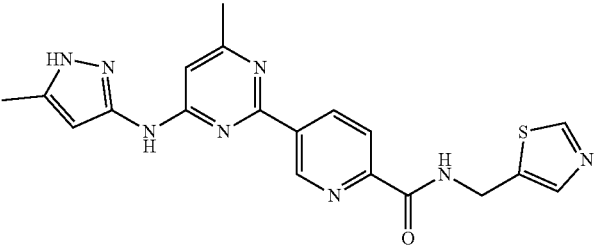 [SMILES: Cc1cc(Nc2cc(C)[nH]n2)nc(-c2ccc(C(=O)NCc3cncs3)nc2)n1] |
| 4 | 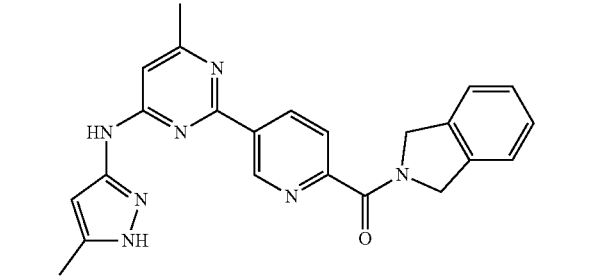 [SMILES: Cc1cc(Nc2cc(C)[nH]n2)nc(-c2ccc(C(=O)N3Cc4ccccc4C3)nc2)n1] |
| 5 | 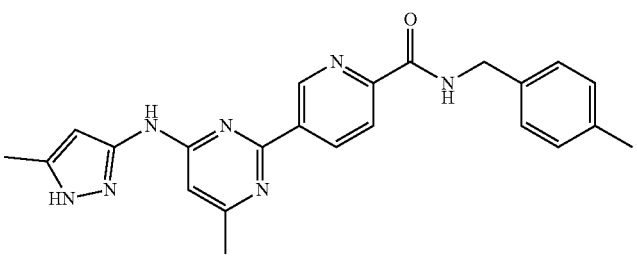 |
| 6 | 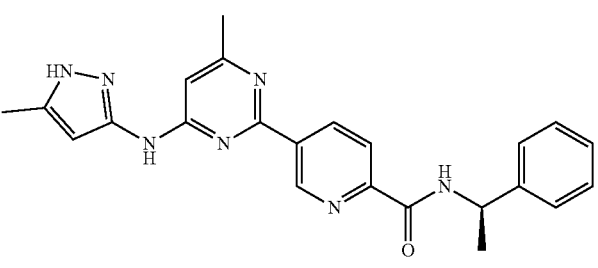 [SMILES: Cc1cc(Nc2cc(C)[nH]n2)nc(-c2ccc(C(=O)N[C@H](C)c3ccccc3)nc2)n1] |

| Compound | Structure |
|---|---|
| 7 | ![Structure of compound 7: 5-methyl-1H-pyrazol-3-ylamino pyrimidine (6-methyl) linked to pyridine-2-carboxamide with N-((5-methylpyridin-2-yl)methyl) group] |
| 8 | ![Structure of compound 8: 5-methyl-1H-pyrazol-3-ylamino-6-methylpyrimidine linked to pyridine-2-carboxamide with N-(3-fluorobenzyl) group] |
| 9 | ![Structure of compound 9: 5-methyl-1H-pyrazol-3-ylamino-6-methylpyrimidine linked to pyridine-2-carboxamide with N-(4-fluorobenzyl) group] |
| 10 | ![Structure of compound 10: 5-methyl-1H-pyrazol-3-ylamino-6-methylpyrimidine linked to pyridine-2-carboxamide with N-(4-methoxybenzyl) group] |
| 11 | ![Structure of compound 11: 5-methyl-1H-pyrazol-3-ylamino-6-methylpyrimidine linked to pyridine-2-carboxamide with N-(4-chlorobenzyl) group] |
| 12 | ![Structure of compound 12: 5-methyl-1H-pyrazol-3-ylamino-6-methylpyrimidine linked to pyridine-2-carboxamide with N-(4-ethoxybenzyl) group] |

-continued

| Compound | Structure |
|---|---|
| 13 | 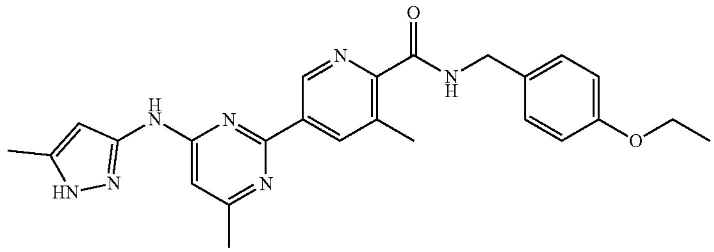 [SMILES: CCOc1ccc(CNC(=O)c2ncc(-c3nc(C)cc(Nc4cc(C)[nH]n4)n3)cc2C)cc1] |
| 14 | 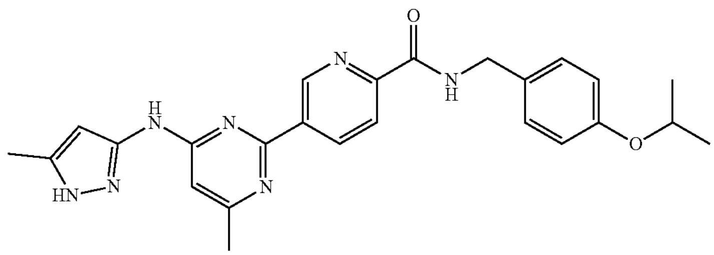 [SMILES: Cc1cc(Nc2cc(C)[nH]n2)nc(-c2ccc(C(=O)NCc3ccc(OC(C)C)cc3)nc2)n1] |
| 15 | 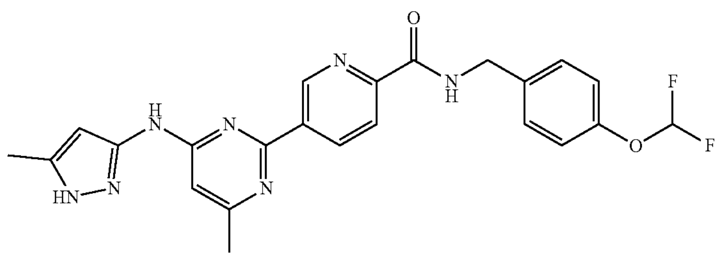 [SMILES: Cc1cc(Nc2cc(C)[nH]n2)nc(-c2ccc(C(=O)NCc3ccc(OC(F)F)cc3)nc2)n1] |
| 16 | 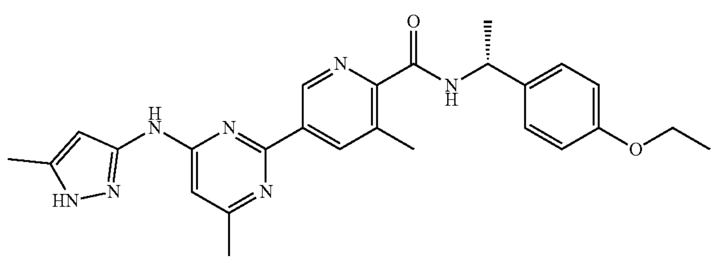 [SMILES: CCOc1ccc([C@@H](C)NC(=O)c2ncc(-c3nc(C)cc(Nc4cc(C)[nH]n4)n3)cc2C)cc1] |
| 17 | 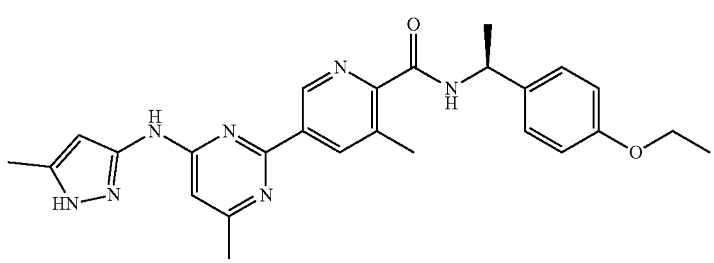 [SMILES: CCOc1ccc([C@H](C)NC(=O)c2ncc(-c3nc(C)cc(Nc4cc(C)[nH]n4)n3)cc2C)cc1] |
| 18 | 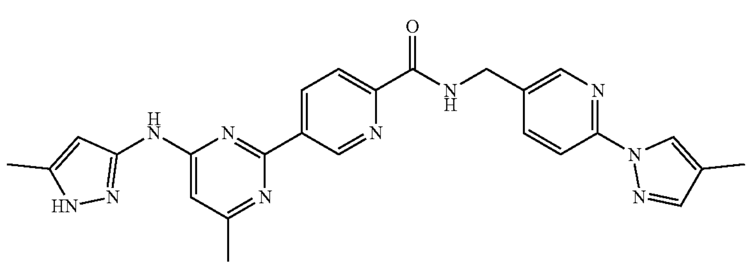 |

| Compound | Structure |
|---|---|
| 19 | (structure) |
| 20 | (structure) |
| 21 | (structure) |
| 22 | (structure) |
| 23 | (structure) |
| 24 | (structure) |

| Compound | Structure |
|---|---|
| 25 | (structure) |
| 26 | (structure) |
| 27 | (structure) |
| 28 | (structure) |
| 29 | (structure) |
| 30 | (structure) |

| Compound | Structure |
|---|---|
| 31 | (structure) |
| 32 | (structure) |
| 33 | (structure) |
| 34 | (structure) |
| 35 | (structure) |

15. A pharmaceutical composition comprising a compound of claim 1 or a pharmaceutically acceptable salt thereof and a pharmaceutically acceptable carrier.

* * * * *